United States Patent
Ogata et al.

(10) Patent No.: US 7,363,070 B2
(45) Date of Patent: Apr. 22, 2008

(54) BIOMAGNETIC MEASUREMENT APPARATUS

(75) Inventors: Kuniomi Ogata, Hachioji (JP); Akihiko Kandori, Kokubunji (JP); Tsuyoshi Miyashita, Fuchu (JP); Keiji Tsukada, Okayama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 593 days.

(21) Appl. No.: 10/875,281

(22) Filed: Jun. 25, 2004

(65) Prior Publication Data

US 2005/0148844 A1   Jul. 7, 2005

(30) Foreign Application Priority Data

Dec. 10, 2003   (JP) ............................. 2003-317705

(51) Int. Cl.
*A61B 5/05* (2006.01)
(52) U.S. Cl. .................. 600/409; 382/128; 324/244
(58) Field of Classification Search ............... 324/244, 324/248, 302; 600/409; 382/128
See application file for complete search history.

(56) References Cited

U.S. PATENT DOCUMENTS

| | | | | | |
|---|---|---|---|---|---|
| 4,977,866 | A | * | 12/1990 | Wilkins ................. | 123/184.34 |
| 5,285,385 | A | * | 2/1994 | Igarashi et al. ............. | 600/409 |
| 5,408,178 | A | * | 4/1995 | Wikswo et al. ............. | 324/201 |
| 5,495,849 | A | * | 3/1996 | Hayashi et al. ............. | 600/409 |
| 5,594,849 | A | * | 1/1997 | Kuc et al. .................... | 345/632 |
| 6,187,032 | B1 | * | 2/2001 | Ohyu et al. ................. | 600/409 |
| 6,374,131 | B1 | * | 4/2002 | Tomita et al. ............. | 600/409 |
| 6,522,908 | B1 | * | 2/2003 | Miyashita et al. .......... | 600/409 |
| 6,941,165 | B2 | * | 9/2005 | Nakai et al. ................. | 600/509 |
| 2003/0063088 | A1 | * | 4/2003 | Machida et al. ............ | 345/440 |

OTHER PUBLICATIONS

H. Hosaka, "Visual determination of generators of the magnetocardiogram", J. ELECTROCARDIOL., vol. 9, 1976, pp. 426-432.

T. Miyashita et al, "Construction of tangential vectors from normal cardiac magnetic field components", Proc. 20th Int. Conf. IEEE/EMBS (Hong Kong), 1998, pp. 520-523.

K. Tsukada et al, "Noninvasive visualization of multiple simultaneously activated regions on torso magnetocardiographic maps during ventricular depolarization", J. Electrocardiol., vol. 32, No. 4, 1999, pp. 305-313.

Y. Yamada et al, "Noninvasive diagnosis of arrythymic foci by using magnetocardiogram-method and accuracy of magneto-anatomical mapping system", Journal Arrhythmia, vol. 16, No. 5, 2000, pp. 580-586.

(Continued)

*Primary Examiner*—Ruth S. Smith
*Assistant Examiner*—Jonathan Cwern
(74) *Attorney, Agent, or Firm*—Mattingly, Stanger, Malur & Brundidge, P.C.

(57) ABSTRACT

Disclosed herein is a biomagnetic measurement apparatus capable of visualizing cardiac electrical current distributions with information on the cardiac morphology of a subject. A magnetic field component in the z direction, vertical to the chest surface of a subject, is measured from two directions, front and back of the chest, and then to calculate the current distributions in the two directions and the distributions of the amplitudes of those current distributions. A three-dimensional standard heart model is created from average data on the cardiac morphology obtained from plural healthy subjects. An optimal position of the model is determined using the coordinates of the sinus node and the coordinates of the left ventricle. Then, a weight coefficient is obtained by front and back current distributions and front and back the distributions of the amplitudes of those current distributions on a set boundary of the model.

17 Claims, 20 Drawing Sheets

OTHER PUBLICATIONS

A. Kandori et al, "A method for detecting myocardial abnormality by using a current-ratio map calculated from an exercise-induced magentocardiogram", Med. Biol. Eng., Comp., vol. 39, 2001, pp. 29-34.

K. Ogata et al, "Visualization method of current distribution in cardiac muscle using a heart model, Transactions of the Japanese Society for Medical and Biological Engineering", vol. 41, No. 1, 2003, pp. 25-33.

* cited by examiner

BIOMAGNETIC MEASUREMENT APPARATUS

CLAIM OF PRIORITY

The present application claims priority from Japanese application JP 2003-317705 filed on Sep. 10, 2003, the content of which is hereby incorporated by reference into this application.

FIELD OF THE INVENTION

The present invention relates to a biomagnetic measurement apparatus that uses superconducting quantum interference device (SQUID) magnetometers to measure a weak magnetic field generated from a human heart.

BACKGROUND OF THE INVENTION

Visualizing electrophysiological phenomena to occur in heart muscles is very important for diagnosing heart diseases such as ischemic heart diseases and arrhythmia. As one of the apparatuses that can visualize such electrophysiological phenomena, there is a biomagnetic measurement apparatus. The biomagnetic measurement apparatus can measure a weak magnetic field (heart magnetic field, hereinafter) generated from a human heart in a noninvasive and yet non-contact manner at many measurement points. The data obtained from such a cardiac magnetic field can be used to visualize the distribution of each current flow in the heart muscles.

As one of the methods for visualizing cardiac electrical current distributions obtained by using the biomagnetic measurement apparatus, a current-arrow map (CAM, hereinafter,) is being under development (see, Non-patent Documents 1 and 2). The CAM is used to define a vector on a two-dimensional plane, which is obtained by differentiating a normal component of cardiac magnetic field data measured at each measurement point. Calculating each CAM from the cardiac magnetic field data obtained by the measurement at front and back regions of a person being tested (subject, hereinafter) makes it possible to visualize the state of the heart muscle action potential propagation of the subject's whole heart (see, Non-patent Document 3). As typical analytical methods for heart diseases using this CAM, there are visualization of abnormal action potential propagation from time-series images of a CAM, and identification of an ischemic region using the CAM in a ventricle depolarization process. With regard to these, there have been many reports saying its effectiveness of such visualization in clinical diagnoses (see, Non-patent Documents 4 and 5).

In recent years, there has been developed a method for projected CAM (PCAM, hereinafter) on a three-dimensional heart model created from images obtained by a nuclear magnetic resonance imaging apparatus (MRI images, hereinafter) of each subject. There also have been reported some methods that make it possible to easily understand visualized cardiac electrical current distributions (see, Non-patent Document 6).

[Non-patent Document 1] H. Hosaka, et al., "Visual determination of generators of the magnetocardiogram," J. Electrocardiol., vol. 9, pp. 426-432, 1976

[Non-patent Document 2] T. Miyashita, et al., "Construction of tangential vectors from normal cardiac magnetic field components," Proc. 20th Int. Conf. IEEE/EMBS (Hong Kong), pp. 520-523, 1998

[Non-patent Document 3] K. Tsukada, et al., "Noninvasive visualization of multiple simultaneously activated regions on torso magnetocardiographic maps during ventricular depolarization," J. Electrocardiol., vol. 32, no. 4, pp. 305-313, 1999

[Non-patent Document 4] Y. Yamada, et. al., "Noninvasive diagnosis of arrhythmic foci by using magnetocardiogram-method and accuracy of magneto-anatomical mapping system-," J. Arrhythmia, vol. 16, no. 5, pp. 580-586, 2000

[Non-patent Document 5] A. Kandori, et. al., "A method for detecting myocardial abnormality by using a current-ratio map calculated from an exercise-induced magnetocardiogram," Med. Biol. Eng. Comput., vol. 39, pp. 29-34, 2001

[Non-patent Document 6] K. Ogata, et. al., "Visualization method of current distribution in cardiac muscle using a heart model," Transactions of the Japanese society for medical and biological engineering, vol. 41, no. 1, pp. 25-33 (2003)

As described above, two-dimensional current distribution maps obtained by using CAMs are projected on the three-dimensional heart model of each subject to obtain visually-apparent images of cardiac electrical current. Such visualized images will make it possible for doctors and clinical laboratories technicians to easily understand analytical results, and also for them to provide their patients with these easy-to-understand analytical results. However, when applying such a method actually, there are two problems coming to arise. The first problem is that MRI and X-ray CT images need to be obtained for each subject, making it time-consuming job to obtain a PCAM from the images. The second problem is that because the base level between CAM current values obtained from the front and back measurement regions depends on a distance between the heart and the measurement surface (front or back), discontinuous values occurs in PCAM at a junction between the front and back surface of the heart model measurement regions.

SUMMARY OF THE INVENTION

Under such circumstances, the primary object of the present invention is to provide a biomagnetic measurement apparatus capable of projecting the current distributions at front and back measurement regions and the distributions of the amplitudes of those current distributions, on a three-dimensional standard heart model seamlessly, and thereby visualizing the cardiac electrical current distributions conforming to the cardiac morphology.

One aspect of the invention is directed to the biomagnetic measurement apparatus which comprises a plurality of magnetometers, each of which is disposed two-dimensionally at a position denoted by the (x, y) coordinates in parallel to the chest surface of the subject and used to measure a time change of a magnetic field component in the z direction vertical to the xy plane of the biomagnetic field generated from the subject's heart from two opposing directions; a calculating device for calculating each output signal from the plurality of magnetometers; and a displaying device for displaying a result of the calculation.

In this aspect, the calculating device performs at least one of:

(1) calculations to obtain current distributions in the two directions from the output signals and/or to obtain distributions of the amplitudes of those current distributions;

(2) a calculation to obtain an isointegral map according to the output signals in a predetermined period (e.g., a T-wave appearing period), and to obtain a region having an isointegral map value exceeding a predetermined threshold value;

(3) a calculation to estimate the moment, direction, and position of one current source, from the output signal at a predetermined point of time (e.g., a P-wave's initial point of time); and (4) at least one calculation selected from the calculations to obtain current distributions in the two directions at the predetermined point of time (e.g., a P-wave's initial point of time) and to obtain distributions of the amplitudes of those current distributions, assuming the moment, direction, and position of the one current source.

The calculating device sets a virtual extended region in which existence of a plurality of magnetometers is assumed on the same disposing condition as that of the plurality of magnetometers in the measurement region, outside the measurement region of the biomagnetic field, to obtain output signals from the plurality of magnetometers in the extended region through extrapolation of the output signals from the plurality of magnetometers, and then makes at least one of the calculations in the steps of (1) to (4).

In another aspect, the calculating device performs:

(5) a calculation to convert data so as to determine an optimal position for displaying the data that represents a three-dimensional heart model simulating a heart shape, and current distributions in the two directions and/or distributions of the amplitudes of those current distributions obtained in the calculation (1), using the result obtained from at least one of the calculations (1) to (4);

(6) a calculation to adjust the base levels of current values into one with respect to the position-adjusted current distributions in the two directions and/or distributions of the amplitudes of those current distributions; and (7) a calculation to obtain synthesized image data obtained by projecting the base-level-adjusted current distributions in the two directions and/or the distributions of the amplitudes of those current distributions, from the z direction, on a position denoted by the (x, y) coordinates of the data representing the three-dimensional heart model.

In still another aspect, in the above calculation (5), the calculating device performs one of the following processings of:

(5a) adjusting the position of the sinus node and the estimated position of the current source so as to minimize the difference (first difference) between those positions in the data for representing a three-dimensional heart model;

(5b) adjusting the positions of the left ventricle region and a region having an isointegral map exceeding a threshold value so as to minimize the difference (second difference) between the left ventricle region and the region having the isointegral map exceeding the threshold value in the data for representing the three-dimensional heart model;

(5c) adjusting the position of the sinus node and the estimated position of the current source, as well as the positions of the left ventricle region and the region having an isointegral map value exceeding a predetermined value so as to minimize the first difference in (5a) and the second difference in (5b); and (5d) adjusting the positions of the current distributions in two directions obtained from (1) and/or distributions of the absolute values of those current distributions by changing the assumption of the moment, direction, and position of one current source in the above (4) so as to minimize the difference between the positions of the current distributions in two directions obtained from (1) and/or distributions of the absolute values of those current distributions.

In yet another aspect, in the above calculation (6), the calculating device performs one of the following processings of:

(6a) obtaining a weight coefficient for enabling the current distributions in two directions obtained in the (1) and/or the distributions of the amplitudes of those current distributions to be aligned most with each other at the position denoted by the (x, y) coordinates of the boundary data of the outermost frame of the data for representing a three-dimensional heart model viewed from the z direction.

(6b) obtaining a weight coefficient for enabling the current distributions in two directions obtained in the above (1) and/or the distributions of the amplitudes of those current distributions to be aligned most with each other at the above boundary.

The synthesized data is displayed on the display device two-dimensionally or three-dimensionally. The display device includes selection buttons for selecting execution of the corresponding calculations in the above (1) to (4) on its screen and executes a calculation corresponding to a button selected by the operator. The display device also displays signals output from the plurality of magnetometers together with the synthesized image data. The display device also displays the synthesized image data three-dimensionally together with the name of each tissue of the heart on the three-dimensional synthesized image.

The display device obtains synthesized image data projected from the z direction by calculation at the position denoted by the (x, y) coordinates of the data for representing a three-dimensional heart model so as to continue the current distributions in two directions obtained in the above (1) and/or the distributions of the amplitudes of those current distributions.

In further aspect, the display device displays:

(8) synthesized image data viewed from an arbitrary direction and at an arbitrary viewpoint two-dimensionally or three-dimensionally;

(9) synthesized image data viewed from both plus and minus directions of the z direction two-dimensionally or three-dimensionally; and

(10) synthesized image data viewed from both plus and minus directions of the x direction two-dimensionally or three-dimensionally.

According to the invention, it is possible to determine an optimal position of a standard heart model for healthy subjects and subjects with heart disease from the cardiac magnetic field data and to obtain a three-dimensional cardiac-current distribution image that includes cardiac morphology information without requiring any of MRI and X-ray CT measurements. It is also possible to adjust the base levels of current values into one so as to link both front and back CAMs continuously and project the current distribution at the front side and the distribution of the amplitude of the current distribution, as well as the weighted back side current distribution and the distribution of the amplitude of the current distribution on the standard heart model or heart model of each subject, thereby obtaining continuous three-dimensional cardiac-current distribution images over the whole heart.

DETAILED DESCRIPTION OF THE PREFERRED EMBODIMENTS

Hereunder, the preferred embodiments of the present invention will be described in detail with reference to the accompanying drawings.

Figure 1:
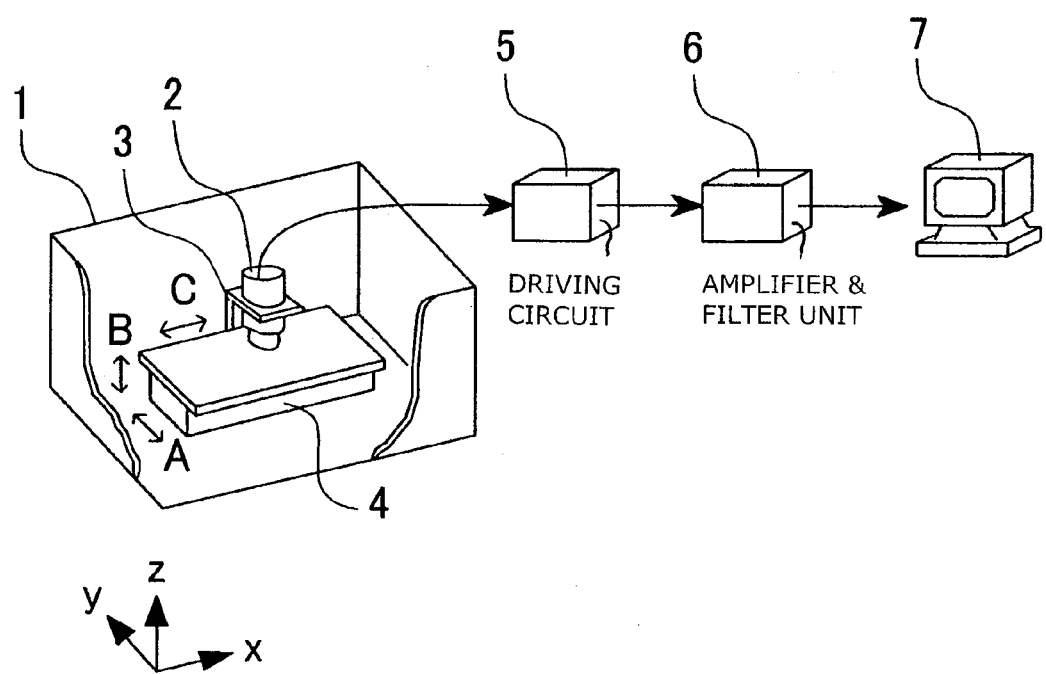
FIG. 1 illustrates a configuration of a biomagnetic measurement apparatus in an embodiment of the invention.

FIG. 1 is a block diagram of a biomagnetic measurement apparatus in an embodiment of the invention.

As shown in FIG. 1, a gantry 3 for retaining a cryostat 2 that retains SQUID magnetometers at an extreme low temperature, as well as a bed 4 on which a subject (not shown) is to lie down are disposed inside a magnetically shielded room 1. The bed 4 is movable on its short axis (A and y directions) and on its long axis (C and x directions), as well as in the up and down directions (B and z directions). Outside the magnetically shielded room 1 are disposed a driving circuit 5 for driving the SQUID magnetometers disposed in the cryostat 2, an amplifier & filter unit 6 for amplifying and filtering the output from the driving circuit 5, and a computer 7 for conducting data-acquisition of output signals from the amplifier & filter unit 6, computation of the collected data, and control for each part of the apparatus.

Figure 2:
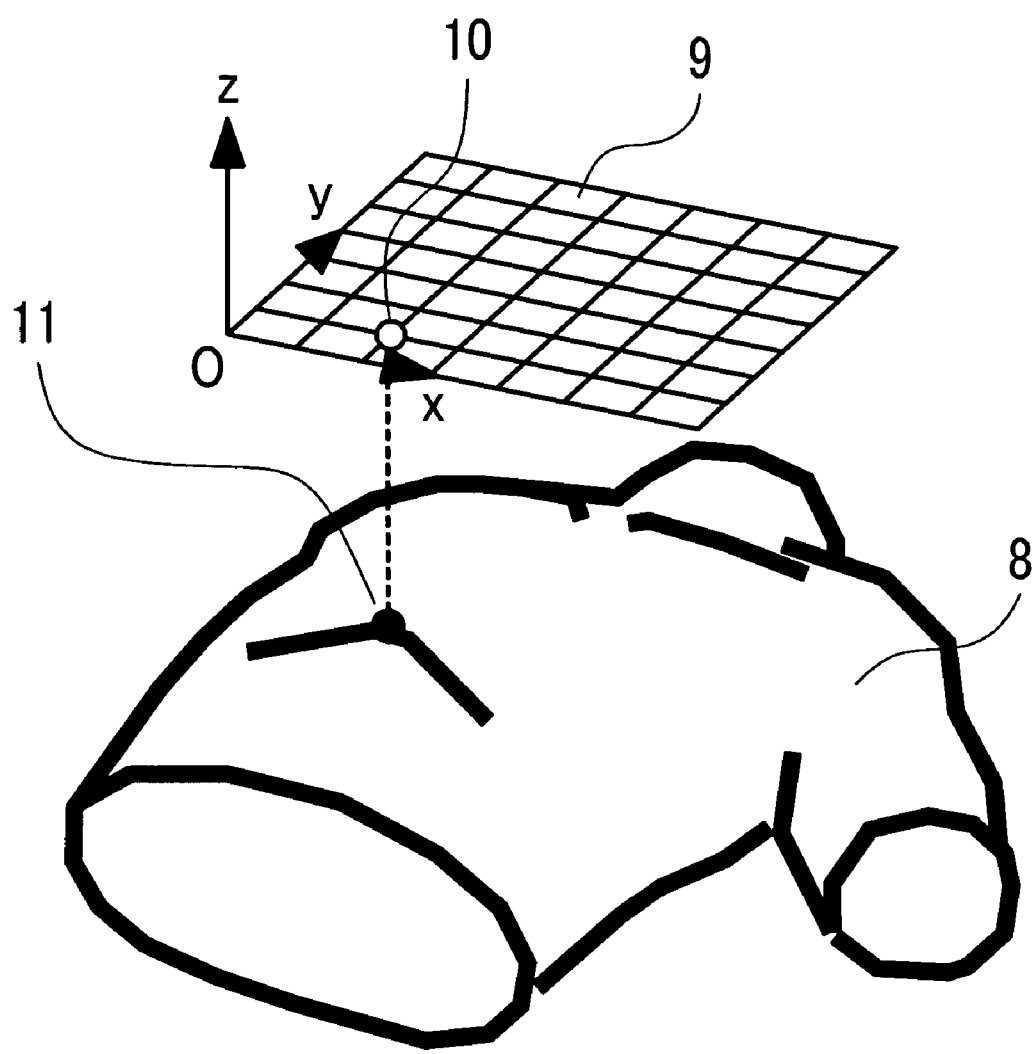
FIG. 2 illustrates a positional relationship between disposition of SQUID magnetometers and a subject when a cardiac magnetic field from a chest surface (front side) of the subject in the biomagnetic measurement apparatus in the embodiment of the invention is measured.

FIG. 2 illustrates the biomagnetic measurement apparatus of this embodiment of the invention. The figure shows a positional relationship between the disposed SQUID magnetometers and a subject when a cardiac magnetic field from the chest surface (front) of a subject is measured. The SQUID magnetometers are so disposed in the cryostat 2 as to be at 25 mm pitches in an 8×8 matrix. In the measurement for the chest surface (front), a cardiac magnetic field measurement region 9 configured by 64 SQUID magnetometers is arranged in parallel to the chest 8 (front side) of the subject and positioned so that the SQUID magnetometer 10 in the 3rd row of the 7th column is placed above the xiphoid process 11 on the chest. The origin of the coordinate system of the measurement region 9 is to be the position of the sensor in the 8th row of the 1st column. The cardiac magnetic field data measured by each SQUID magnetometer is a component Bz vertical to the measurement region 9.

Each of the SQUID magnetometers described above may be replaced with a SQUID magnetometer for detecting a time change of the magnetic field component Bx in the x direction and that of the magnetic field component By in the y direction in parallel to the xy (chest) surface of the biomagnetic field_, respectively. Note that in that case, the current arrows obtained from the magnetic field components Bx and By with use of a well-known method are to be used instead of the current arrows to be described below.

Figure 3:
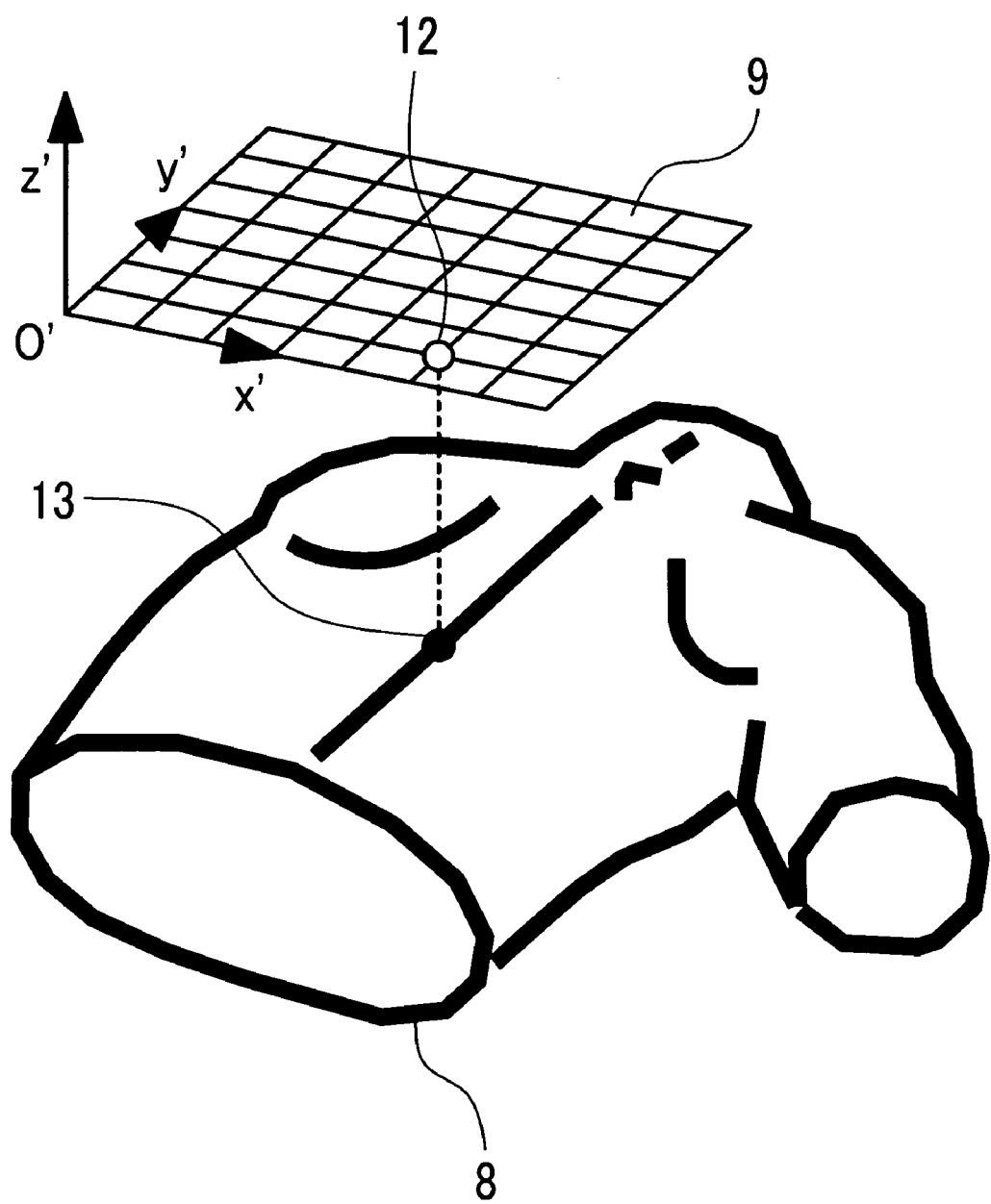
FIG. 3 illustrates a positional relationship between disposition of SQUID magnetometers and a subject when a cardiac magnetic field from the back side of the subject in the biomagnetic measurement apparatus in the embodiment of the invention is measured.

FIG. 3 illustrates the biomagnetic measurement apparatus in this embodiment of the invention. The figure shows a positional relationship between the disposed SQUID magnetometers and the subject when a cardiac magnetic field from the subject's back surface (back side) is measured. The cardiac magnetic field measurement region 9 configured by 64 SQUID magnetometers is disposed in parallel to the chest 8 (back side) of the subject and positioned so that the SQUID magnetometer 12 in the 6th row of the 7th column is placed above the position directly behind the xiphoid process 11 of the chest.

Hereunder, a description will be made for an embodiment of the biomagnetic field measurement apparatus capable of projecting current distributions of front and back planes of the subject and distributions of the amplitudes of those current distributions, on a three-dimensional standard heart model continuously, and thereby visualizing the cardiac electrical current distributions conforming to the cardiac morphology.

First Embodiment

In this first embodiment, an average value of the sizes of the hearts for three healthy subjects is used to create a three-dimensional standard heart model to be applied to a plurality of subjects. Although a standard heart model is created from image data of three healthy subjects in this first embodiment, it is also acceptable to create the model from the image data of only one healthy subject or those of two or more healthy subjects.

Figure 4:
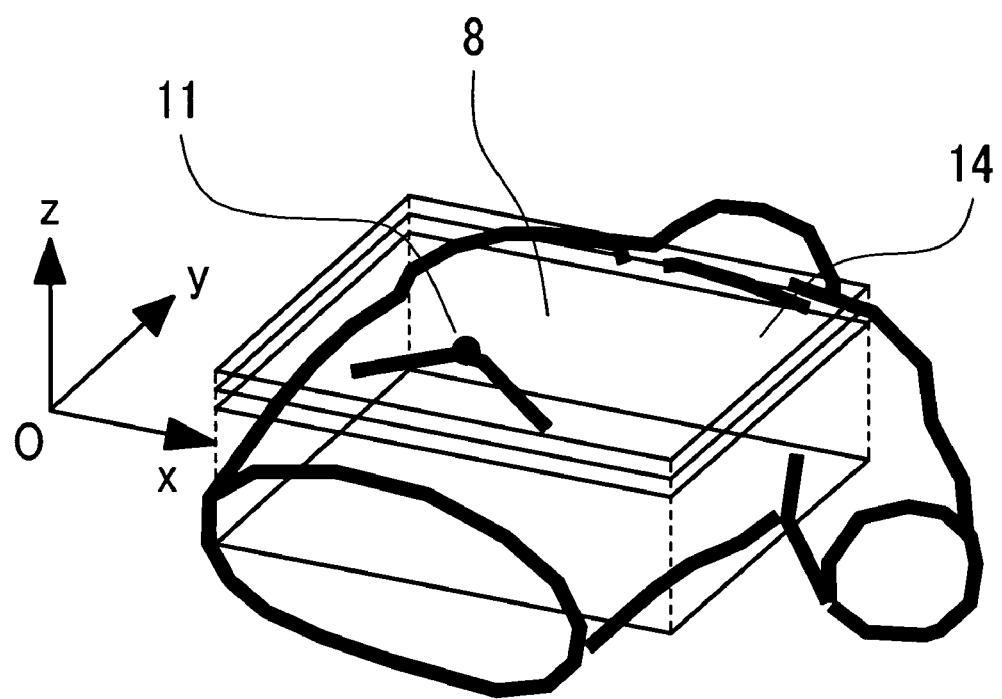
FIG. 4 illustrates a measurement region of a nuclear magnetic resonance imaging apparatus in the first embodiment of the invention.

FIG. 4 explains the first embodiment by illustrating a measurement region of a nuclear magnetic resonance imaging apparatus (MRI apparatus, hereinafter). The measurement region 14 of the MRI apparatus is defined as a 300 mm×300 mm region located on the coronal plane of the chest wall (front side) of the subject. In order to visualize a three-dimensional heart structure, the measurement region 14 is moved in steps of 5 mm on the z axis to obtain MRI images of 1 mm in slice thickness. The standard heart model is created in the following steps of (1) to (3).

(1) The heart outline points are extracted from the MRI images of each of the three subjects to create a three-dimensional heart model.

(2) The centroid of the three-dimensional heart model of each subject is calculated to obtain a distance from the centroid to each outline point.

(3) An average distance from the centroid to each outline point is calculated from the three-dimensional models of the three subjects. From this average distance, the three-dimensional standard heart model is prepared. Then, the sizes of the hearts for the three subjects are averaged to create the three-dimensional standard heart model.

Figure 5:
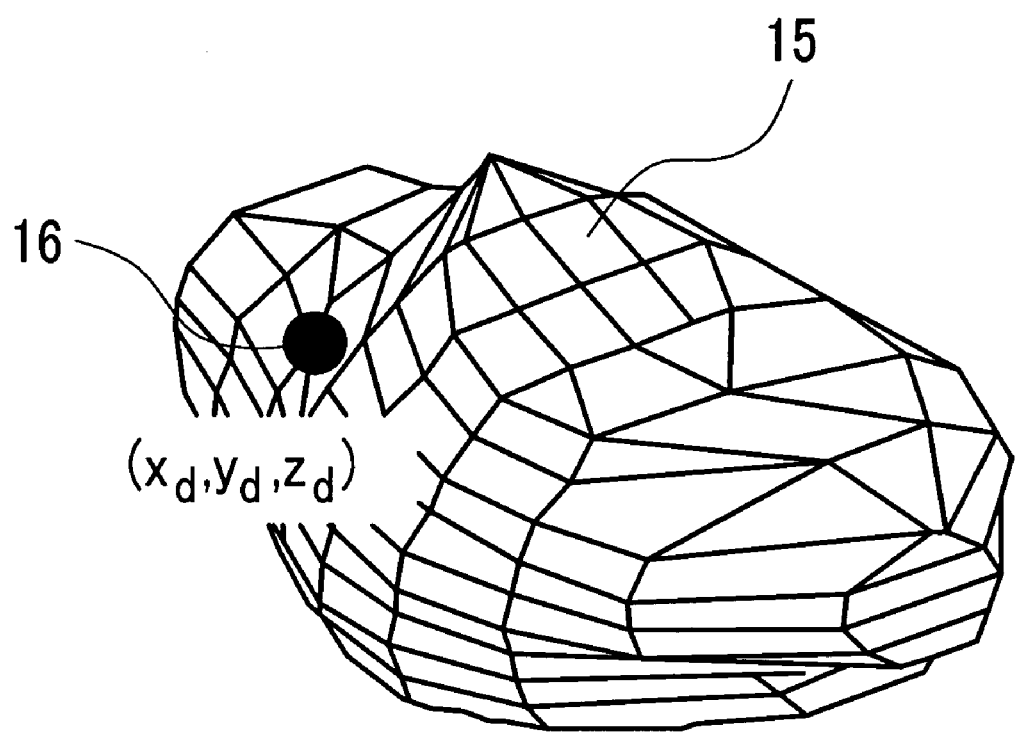
FIG. 5 illustrates a three-dimensional standard heart model obtained by averaging the sizes of the hearts of three subjects in the first embodiment of the invention.

FIG. 5 illustrates a three-dimensional standard heart model created by averaging the sizes of the hearts for three subjects in the first embodiment of the invention.

Next, a description will be made for the method for determining an optimal position of the standard heart model. To obtain an optimal position of the standard heart model, the coordinates of the sinus node is used as the information on the heart's position. A sinus node is an element (existing in a part between the right atrium and the superior vena cava) that controls the rhythm of the heart. The coordinates of the sinus node can be identified by dipole estimation of the P-wave initial time phase, which is an atrium excitement time phase started by the excitement of the sinus node. The dipole estimation method is a method for estimating the position $(x_d', y_d', z_d')$, the direction $\theta$, and the moment Q of a dipole. It results in the optimization problem that minimizes the result of the expression 1.

$$F_i(x_d',y_d',z_d',\theta,Q)=\Sigma(B_{t,i}-QL_i(x_d',y_d',z_d',\theta))^2/\Sigma(B_{t,i}) \quad (1)$$

Here, $B_{t,i}$ (i=1, 2, . . . , 64) represents a normal component of a magnetic field at a time t, measured by each sensor of the biomagnetic measurement apparatus. The $L_i$ represents a coefficient obtained by the biot-savart's law. The $\Sigma$ placed at each of the numerator and the denominator represents an addition of i=1 to 64. This dipole estimation can be employed to estimate a local cardiac excitation region around the sinus node accurately.

An optimal position of the standard heart model is determined in the following steps of (1) to (3).

(1) As shown in FIG. 5, the coordinates $(x_d, y_d, z_d)$ 16 of the sinus node are set on the standard heart model 15.

Figure 6:
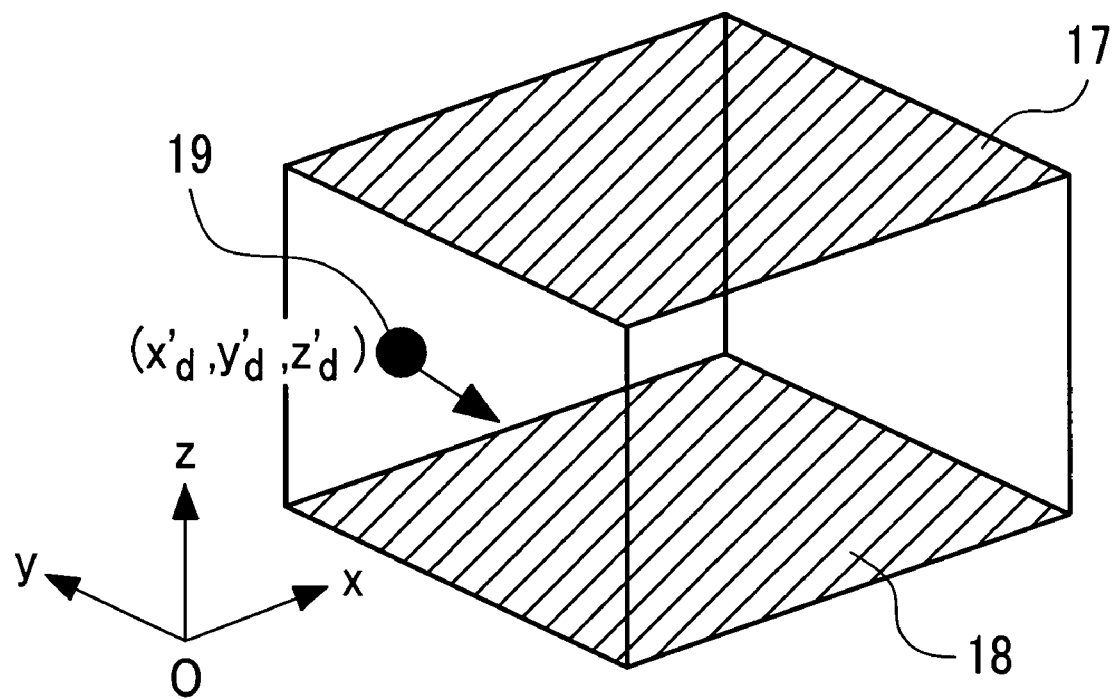
FIG. 6 illustrates a positional relationship between coordinates of estimated current dipole and front and back measurement planes in the first embodiment of the invention.

(2) As shown in FIG. 6, dipole estimation is calculated from the cardiac magnetic field data in the P-wave initial time phase, measured at a measurement surface 17 at the front side or/and at a measurement surface 18 at the back side of the subject, thereby obtain the dipole coordinates 19 $(x_d', y_d', z_d')$.

FIG. 6 illustrates a positional relationship between the measurement surfaces 17 and 18 of the cardiac magnetic field at the front and back planes and the coordinates 19 of the estimated dipole.

(3) The standard heart model 15 is moved to a position where the coordinates of the dipole 19 and the coordinates of the sinus node 16 on the standard heart model 15 come to overlap to each other.

A description will be made for the method for projecting the current distributions at the front and back planes of the subject and the distributions of the amplitudes of those current distributions, on the standard heart model. CAMs herein are used to calculate the current distributions and the distributions of the amplitudes of those current distributions. Note that the CAM is a method used for defining a current arrow (CA, hereinafter) I (x, y) obtained from a space differentiation of a normal component Bz of a magnetic field at each measurement point of the biomagnetic measurement apparatus. CAM is obtained as a projection view onto two-dimensional view. The x and y components of I (x, y) at each measurement point are approximated by the expression 2, and a current distribution amplitude is obtained by the expression 3.

$$I_x(x,y)=dB_z(x,y)/dy \quad I_y(x,y)=-dB_z(x,y)/dx \quad (2)$$

$$|I(x,y)|=\sqrt{\{(I_x(x,y))2+(I_y(x,y))2\}} \quad (3)$$

When CAMs is projected on a standard heart model, the front CAM is projected onto the front surface, and the back CAM is projected onto the back surface of the standard heart model, respectively. However, because the base levels used for the front and back CAM current values are different, if CAMs are projected at front and back surfaces of the standard heart model simply, a discontinuous current distributions comes to appear at a junction between the front and back surfaces of the standard heart model. This is because the distance between the heart and the front measurement surface differs from the distance between the heart and the back measurement surface. To solve this problem, the difference between those base levels is eliminated by adjusting those base levels into one as follows.

Figure 7:
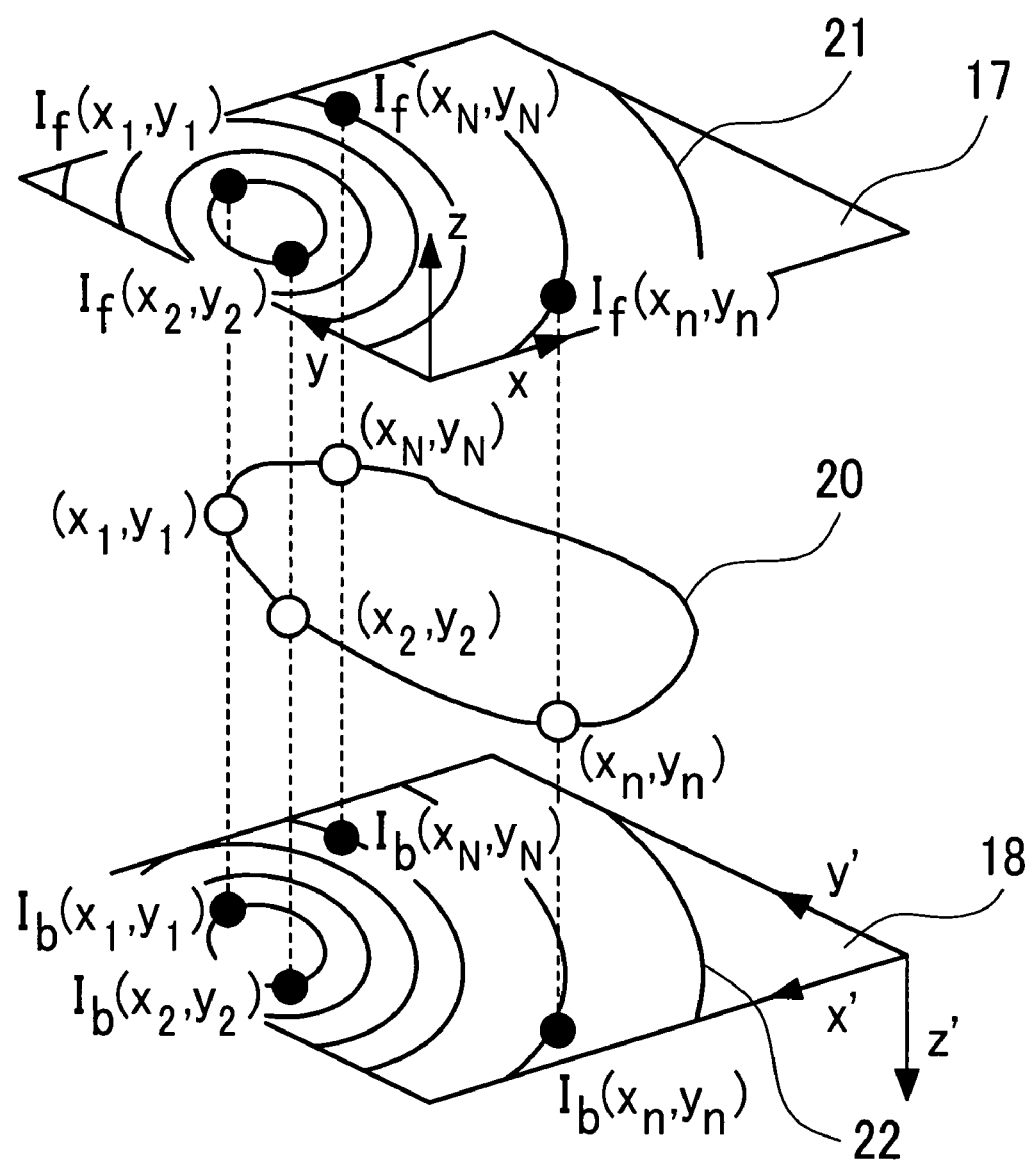
FIG. 7 illustrates the method for calculating a weight coefficient W in the first embodiment of the invention.

FIG. 7 illustrates the method for calculating a weight coefficient W in the first embodiment of the invention.

(1) As shown in FIG. 7, the coordinates 20 $((x_n, y_n), n=1, 2, \ldots, N)$ of the outline of the standard heart model viewed from the coronal plane are extracted.

(2) As shown in FIG. 7, calculations are made, by the expression 3 for the amplitude If $(x_n, y_n)$ of the CA on the front measurement plane 17 (amplitude of the current distribution of the front plane) 21 and for the amplitude $I_b$ $(x_n, y_n)$ of the CA on the back measurement plane 18 (amplitude of the current distribution of the back plane) to be projected onto a place denoted by the coordinates 20 $(x_n, y_n)$.

(3) A calculation is made for a weight coefficient W that minimizes the result of the expression 4 using $I_f(x_n, y_n)$ 21 and $I_b$ $(x_n, y_n)$ 22. Symbol $\Sigma$ in the expression 4 denotes an addition of n=1 to N.

$$F(W)=\Sigma(I_f(x_n,y_n)-W\times I_b(x_n,y_n))^2 \quad (4)$$

(4) The expression 4 is calculated for time over one heartbeat or the total measurement time and optimal weight coefficient is determined by W with minimum value of F(W).

(5) The front CAM and the weighted back CAM are projected onto the standard heart model. Note that CAM interpolation is done near the junction where the front and back CAMs are to be projected in order to obtain continuous current distributions.

Figure 8:
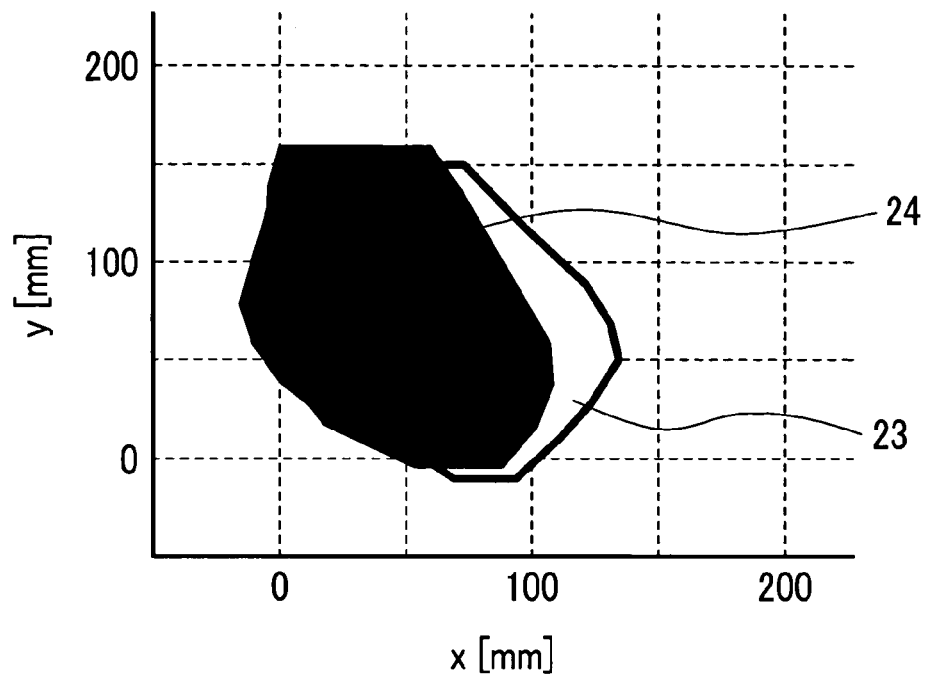
FIG. 8 illustrates a positionally adjusted standard heart model obtained as a result of dipole estimation and a result of optimal position for a healthy subject A in the first embodiment of the invention.

FIG. 8 illustrates a positionally adjusted standard heart model obtained as a results of the dipole estimation result in the first embodiment of the invention. FIG. 8 shows a result of optimal position determination of a standard heart model with respect to a healthy subject A. In FIG. 8, a white region enclosed by a solid line represents a heart region 23 of the subject A, obtained from MRI images. The black region enclosed by another solid line corresponds to the positionally adjusted standard heart model 24. As shown in FIG. 8, this method can place the standard heart model at almost the same position as that of the actual heart.

Figure 9:
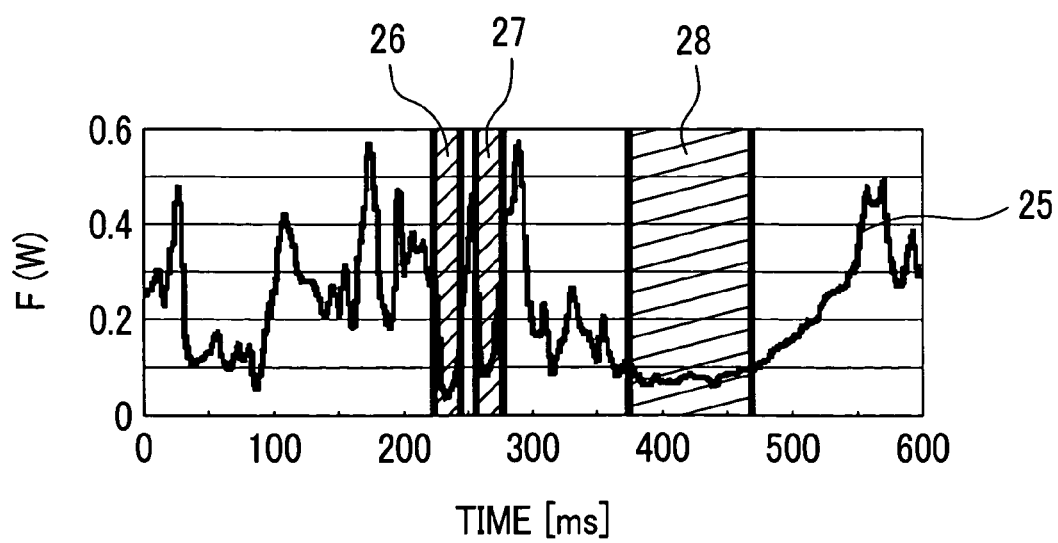
FIG. 9 illustrates an example of an F(W) in a heartbeat period of the healthy subject A in the first embodiment of the invention.

FIG. 9 illustrates an example of the F(W) for one heartbeat of the healthy subject A, in the first embodiment of the invention. As shown in FIG. 9, the F(W) 25 is found to become small stably in the three time phases (beginning of the QRS-complex 26, lasting of the QRS-complex, beginning of the T-wave). In the three time phases, the F(W) becomes the minimum at 236 ms (beginning of the QRS-complex 26). Consequently, the front CAM and weighted back CAM are projected onto the standard heart model.

FIG. 10 shows projection results of weighted current distributions in the first embodiment of the invention. The front CAM and the weighted back CAM at the lasting of the P-wave are projected onto the positionally adjusted standard heart model 29, respectively. FIG. 10A is a back view, FIG. 10B is a front view, FIG. 10C is a right hand side view, and FIG. 10D is a left hand side view of the PCAM. Each arrow in each of FIGS. 10A to 10D denotes a current vector 30 as follows; white region 31 denotes a region in which the amplitude of the current vector is small, gray region 32 denotes a region in which the amplitude of the current vector is medium, black region 33 denotes a region in which the amplitude of the current vector is large, respectively. In FIGS. 10A through 10D, the size of the current vector is represented in three levels to simplify the display. Actually, however, the current vector is divided into 128 or 512 sizes and displayed by a unique color in each size. (This is also the same for FIGS. 11, 13, 20, 21, and 23 to be described later.)

Figure 10A:
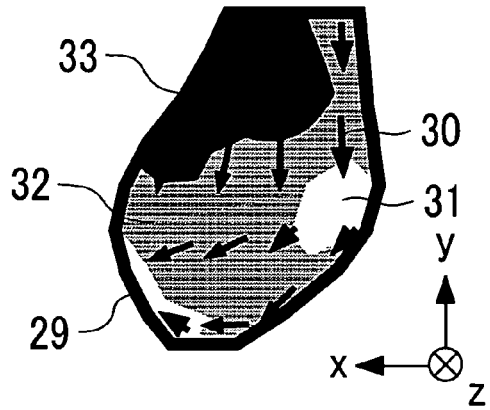
FIG. 10 illustrates a result of projection of front CAM and weighted back CAM on a standard heart model after its optimal position is determined in the first embodiment of the invention.
Figure 10B:
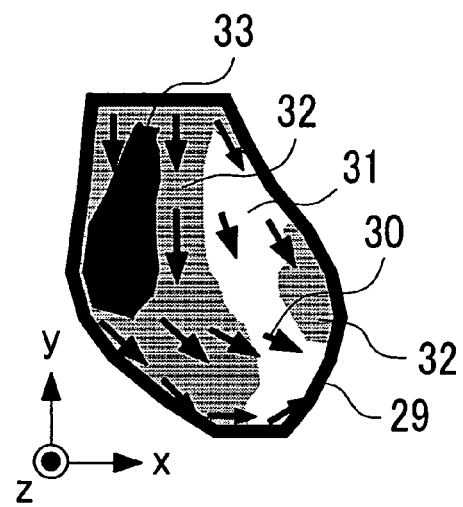
Figure 10C:
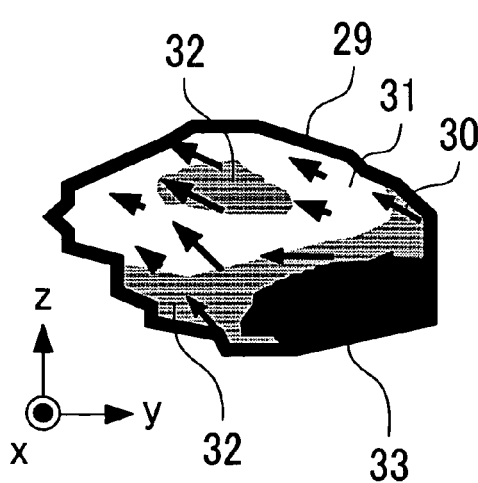
Figure 10D:
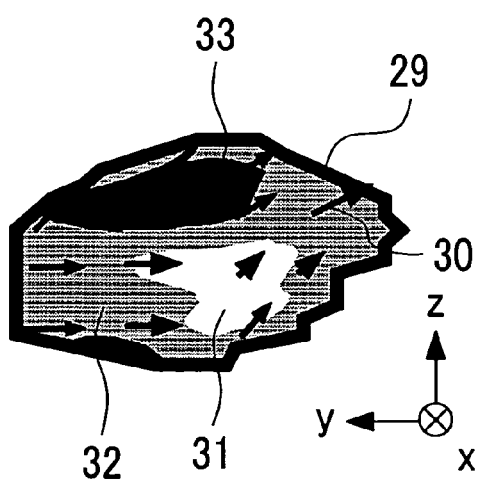

The cardiac excitation at the lasting of the P-wave corresponds to the atrium excitation and the left atrium excitation becomes rather stronger than that in the right atrium. As shown in FIG. 10A and FIG. 10B, a stronger current region is found in each of the right and left atriums. In particular, the excitation region in the left atrium is found to be stronger than that in the right atrium. As shown in FIGS. 10C and 10D, the front CAM and the back CAM that is weighted by a coefficient W are projected onto the standard heart model continuously.

In the first embodiment of the invention, the results of the projections of the front CAM and the back CAM that is weighted by a coefficient W are displayed on the same screen as follows; those shown in FIG. 10A and FIG. 10B that show projection results as viewed from both minus plus directions of the z direction or those shown in FIG. 10C and FIG. 10D that show projection results as viewed from both plus and minus directions of the x direction are displayed on the same screen.

FIG. 11 shows a projection result of current distributions that are not weighted in the first embodiment of the invention. In FIG. 11, the front and the back CAMs at the lasting of the P-wave are projected onto the positionally adjusted standard heart model 29. In other words, FIG. 11 shows a projection result when the base levels of the current values are not adjusted into one yet in the first embodiment of the invention. Both subject and analysis time are the same as those in FIG. 10. FIG. 11A is a back projection view, FIG. 11B is a front projection view, FIG. 11C is a right hand projection view, and FIG. 11D is a left hand projection view of the standard heart model. Each arrow in each of FIGS. 11A through 11D denotes a current vector 34 as follows; white region 35 denotes a region in which the amplitude of the current vector is small, gray region 36 denotes a region in which the amplitude of the current vector is medium, and black region 37 denotes a region in which the amplitude of the current vector is large, respectively.

Figure 11A:
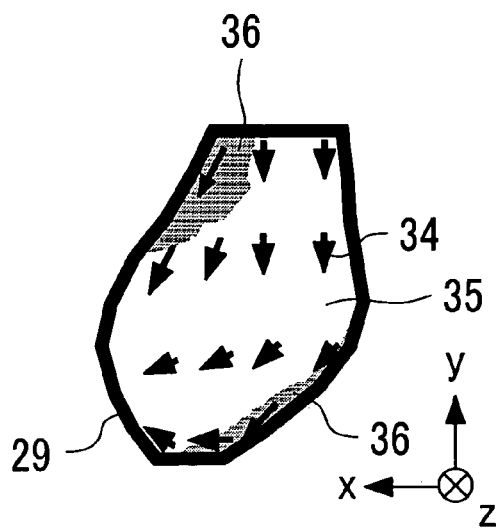
FIG. 11 illustrates a result of projection of current distributions that are not weighted in the first embodiment of the invention.
Figure 11B:
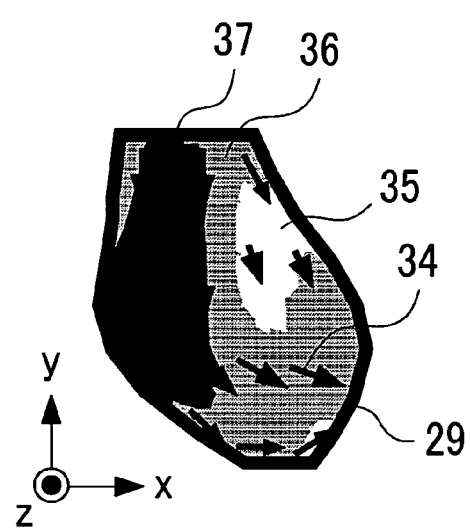
Figure 11C:
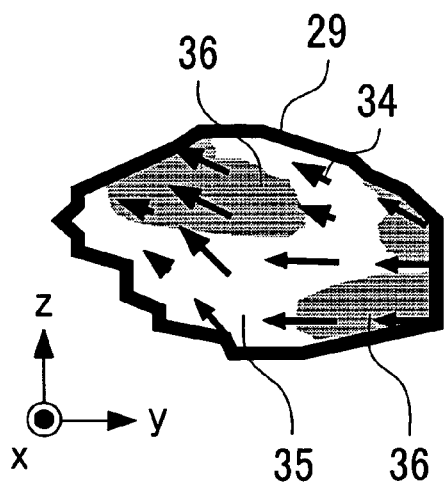
Figure 11D:
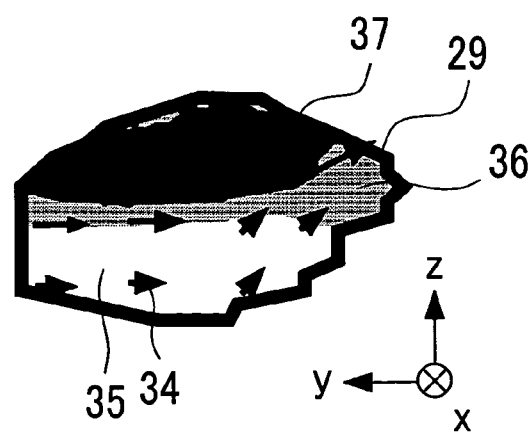

As shown in FIGS. 11A and 11B, large current regions are concentrated in the right atrium and no excitation is recognized in the left atrium. As shown in FIGS. 11C and 11D, discontinuous current distribution occurs at a junction between the front and back surfaces of the standard heart model. Consequently, from the result in FIG. 10, weighted cardiac-current distribution images correspond to the electrophysiological phenomena in the subject heart.

Next, a description will be made for a processing flow in the first embodiment of the invention. At first, a series of processings is started in step 101. Then, the cardiac magnetic fields are measured (at front and back planes of the subject) in step 102. In step 103, current distributions (at front and back sides) are calculated from the measured magnetic fields. In step 104-1, coordinates of the sinus node 16 are set on the standard heart model as described with reference to FIG. 5. Then, in step 105-1, the coordinates of the dipole 19 are calculated (FIG. 6). The coordinates of the dipole are obtained from dipole estimation at the initial time phase of the P-wave. In step 106, an optimal position of the standard heart model is determined using the coordinates of the sinus node 16 set in step 104-1 and the coordinates of the dipole 19 calculated in step 105-1. In step 107, the base levels of current values of the current distributions (at front and back planes of the subject) are adjusted into one as described with reference to FIG. 7. In step 108, the current distributions (at front and back planes) and the distributions of the amplitudes of those current distributions are projected onto the standard heart model, then the projection result is displayed on the screen of the computer 7. Finally, the series of processings ended in step 109.

Figure 13:
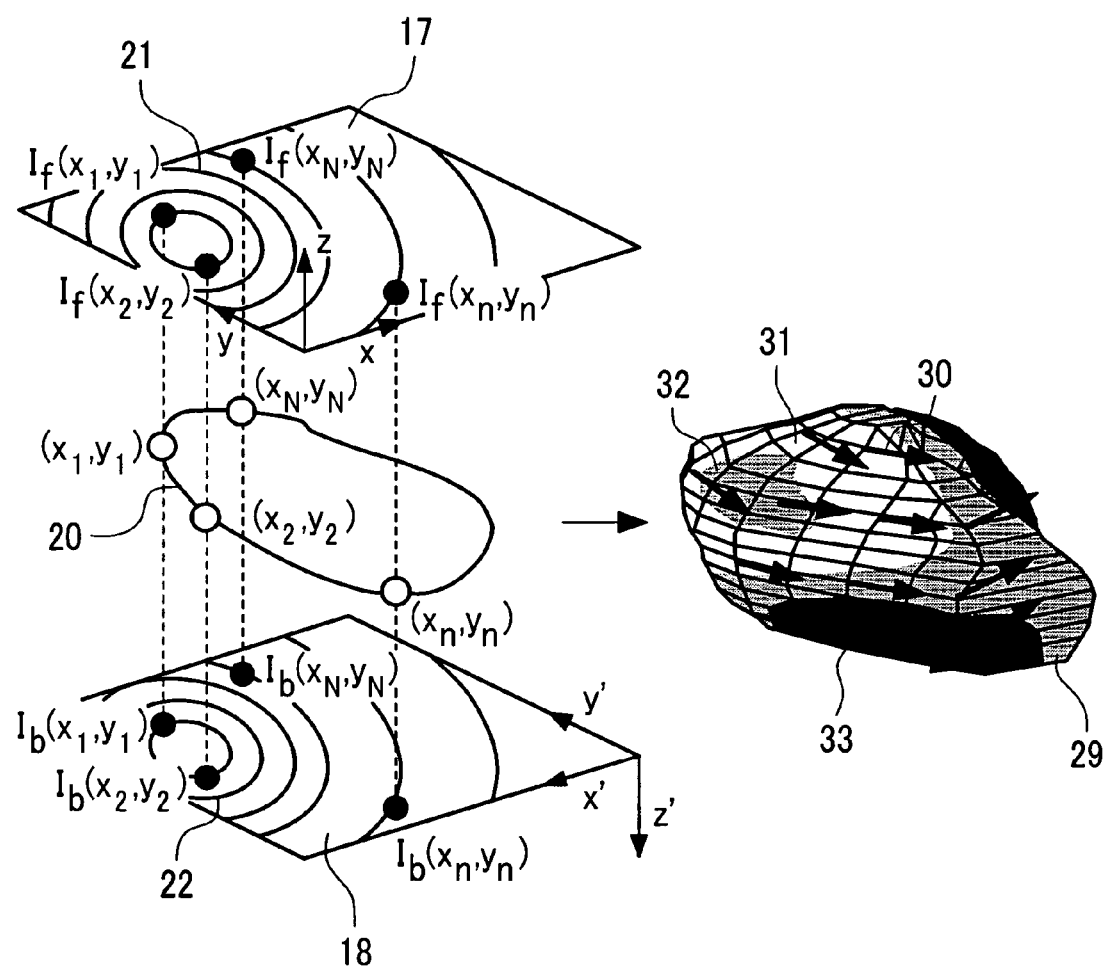
FIG. 13 illustrates a summary of the first embodiment of the invention.

FIG. 13 illustrates the summary of the first embodiment of the invention. The left illustration in FIG. 13 is the same as that shown in FIG. 7. In the first embodiment, the magnetic component in the z direction vertical to the chest surface of the subject is measured from the front 17 and the back 18 measurement planes of the chest and then to calculate the current distributions from the front 17 and back 18 measurement planes date and the distributions 21 and 22 of the amplitudes of those current distributions. A three-dimensional standard heart model is created from the average data obtained from the heart morphology of three healthy subjects, then an optimal position of the standard heart model is determined with respect to each of the three subjects using the coordinates of the subject's sinus node and the coordinates of the subject's left ventricle region.

Furthermore, a calculation is made for a weight coefficient that enables the distributions of the amplitudes of the front and back current distributions on the outline points of the standard heart model, then the base levels of the current values between the current distributions 21 and 22 for the measurement planes and the distributions of the amplitudes of those current distributions are adjusted into one. These weighted current distributions for the measurement planes and the distributions of the amplitudes of those current distributions are projected onto the positionally adjusted standard heart model 29 to thereby obtain the three-dimensional display of the cardiac electrical current distribution image shown at the right side in FIG. 13. In FIG. 13, each arrow denotes a current vector 30 as follows; white region 31 denotes a region in which the vector is small, gray region 32 denotes a region in which the current vector is medium, and black region 33 denotes a region in which the current vector is large, respectively.

As for the three-dimensional display of the cardiac electrical current distribution image in the first embodiment, the base levels of the current value are adjusted into one as described above. This makes it possible to obtain the cardiac electrical current distribution images in accordance with the electrophysiological phenomena in the subject heart.

Second Embodiment

In the second embodiment, an optimal position of the standard heart model is determined using the coordinates of the left ventricle region as the heart position information. The left ventricle is a part that transfers blood to the aorta and its cardiac muscle is the thickest among the regions of cardiac muscle. The coordinates of this left ventricle can be found from an isointegral map of the T-wave that reflects a phase of the ventricle repolarization. The isointegral map mentioned here is obtained by integrating the amplitude of the cardiac electrical current distribution for the arbitrary time interval. An isointegral map can be calculated by the expression 5 using CAMs.

$$I_{sum}(x,y) = \int |I_t(x,y)| dt \qquad (5)$$

The integral section in the expression 5 is between $T_1$ and $T_2$. The $I_t(x, y)$ denotes a CAM at instant time t, which can be calculated by the expression 3. As shown in the expression 5, it is found that an isointegral map corresponds to a total sum of the amplitude of the cardiac electrical current for the arbitrary time interval. Consequently, a region in which the T-wave isointegral map is stronger is assumed to be able to correspond to the left ventricle region having the thickest cardiac muscle and a large cardiac-current. An optimal position of the standard heart model is determined in the following steps of (1) to (4).

Figure 14:
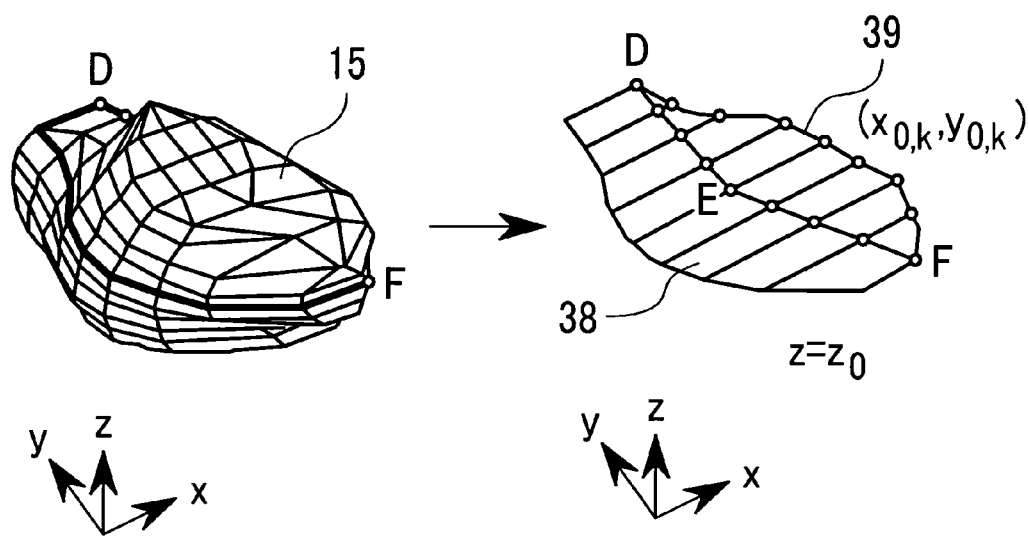
FIG. 14 illustrates a method for extracting the left ventricle region of a three-dimensional standard heart model in the second embodiment of the invention.

FIG. 14 illustrates how to extract the left ventricle region of a three-dimensional standard heart model, in the second embodiment of the invention.

Figure 15:
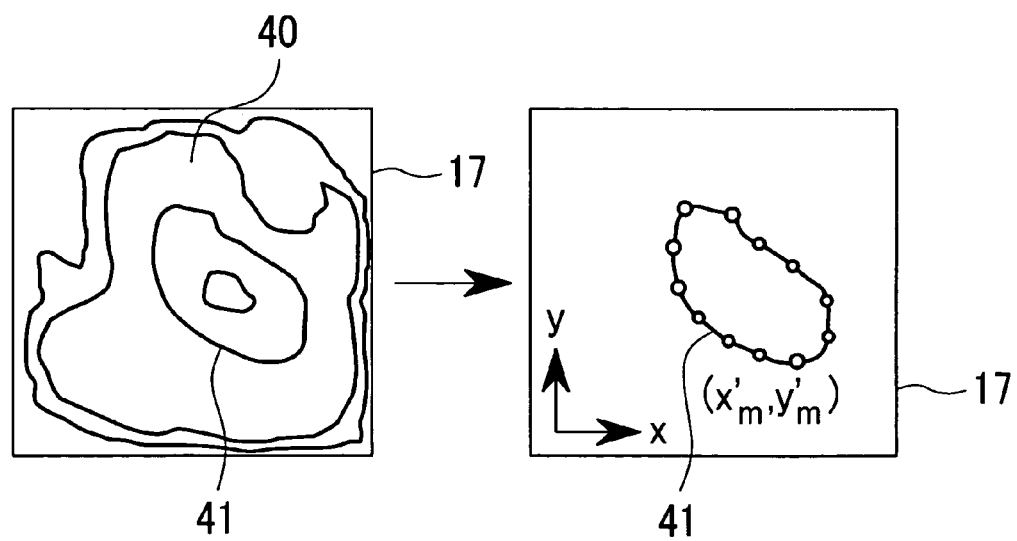
FIG. 15 illustrates a T-wave isointegral map and a method for extracting a region in which an integral value is over a threshold value in the second embodiment of the invention.

FIG. 15 illustrates a method for extracting a region in which integral value is obtained from isointegral map during a T-wave using a threshold value (predetermined threshold value), in the second embodiment of the invention.

(1) As shown in FIG. 14, a two-dimensional region 38 of $Z=Z_0$ is extracted from a three-dimensional standard heart model 15, then the coordinates 39 (($x_{0,k}$, $Y_{0,k}$), k=1, 2, ..., K) of the left ventricle region consisting of DEF points are extracted from the model.

(2) As shown in FIG. 15, an isointegral map 40 during a T-wave is calculated from the expression 5 to extract the coordinates 41 (($x'_m$, $y'_m$), m=1, 2, ..., M) of an isointegral map region having an integral value over a threshold value. Here, M=K is assumed.

(3) A root mean square error $F_2$ is defined as shown in the expression 6. The $F_2$ is represented by a difference between the coordinates ($x_{0,k}$, $y_{0,k}$) 39 of the left ventricle region and the coordinates 41 ($x'_m$, $y'_m$) obtained from the isointegral map 40. Then, the amount of translation ($\Delta x$, $\Delta y$) of the standard heart model that minimizes the $F_2$ is obtained. In the expression 6, $\Sigma$ of each of the numerator and the denominator represents an addition of 1 to K.

$$F_2(\Delta x, \Delta y) = \sqrt{\{\Sigma[(x_{0,k}+\Delta x-'_k)2+(y_{0,k}+\Delta y-y'_k)2]\}} / \sqrt{\{[(x'_k)2+(y'_k)2]\}} \qquad (6)$$

(4) The amount of translation ($\Delta x$, $\Delta y$) of the standard heart model obtained from the expression 6 is used to determine an optimal position of the standard heart model.

As a result, the optimal position of the standard heart model is found to be almost the same as that (FIG. 8) of the standard heart model in the first embodiment. Both front and back CAMs are also projected on the standard heart model just like in the first embodiment. The three-dimensional standard heart model, the front CAM, and the weighted back CAM are synthesized into an image to be displayed and the displayed image in the second embodiment is found to be the same as that in the first embodiment (FIG. 10). As a result, it is found that the second embodiment can also obtain the same effect as that in the first embodiment.

Figure 12:
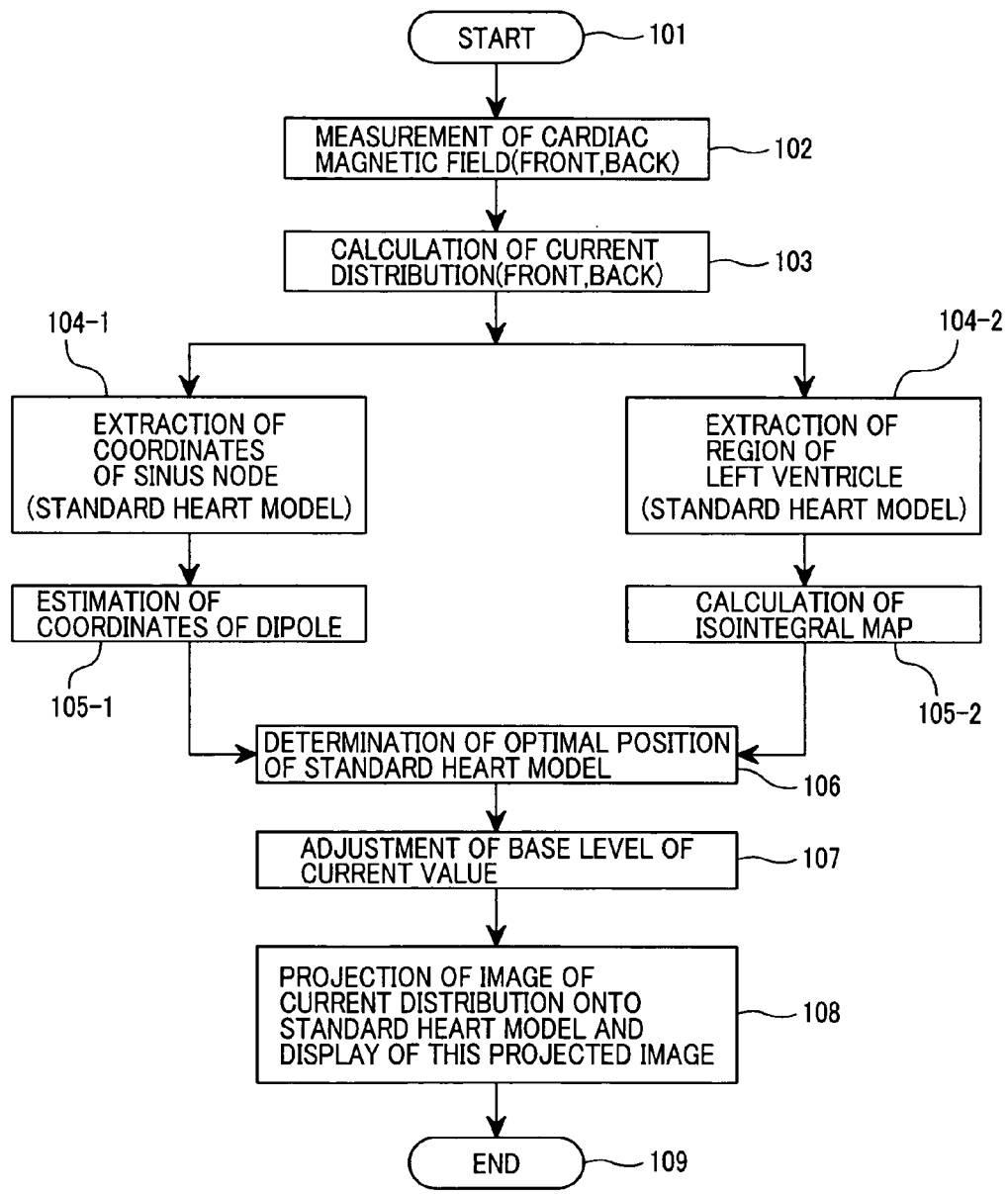
FIG. 12 illustrates a processing flow in each of the first to third embodiments of the invention.

Next, a processing flow in the second embodiment of the invention will be described with reference to FIG. 12. Just like the processing flow in the first embodiment, at first, the processings in steps 101 to 103 are executed. Then, in step 104-2, the coordinates 39 of the left ventricle region are extracted from the three-dimensional standard heart model as described with reference to FIG. 14. In step 105-2, the isointegral map during the T-wave is calculated to extract the coordinates 41 of a region having an integral value over a threshold value, from the isointegral map 40. In step 106, an optimal position of the standard heart model is determined using the coordinates 39 of the left ventricle region extracted in step 104-2 and the coordinates 41 of the isointegral map extracted in step 105-2. The processings in step 106 to 109 are the same as those in the first embodiment, so that the description for them will be omitted here.

Third Embodiment

In this third embodiment 3, an optimal position of the standard heart model is determined using the coordinates of the sinus node and the coordinates of the left ventricle region as the information on the heart's position. The optimal position is determined in the following steps of (1) to (4).

Figure 16:
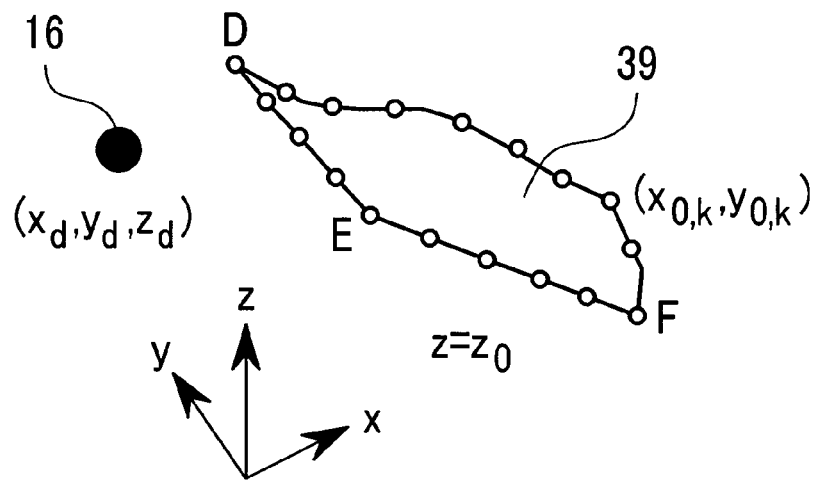
FIG. 16 illustrates a method for extracting the left ventricle region of a three-dimensional standard heart model and a method for setting coordinates of a sinus node on the model in the third embodiment of the invention.

FIG. 16 illustrates a method for extracting the left ventricle region of the three-dimensional standard heart model and a method for setting the coordinates of the sinus node on the standard heart model.

Figure 17:
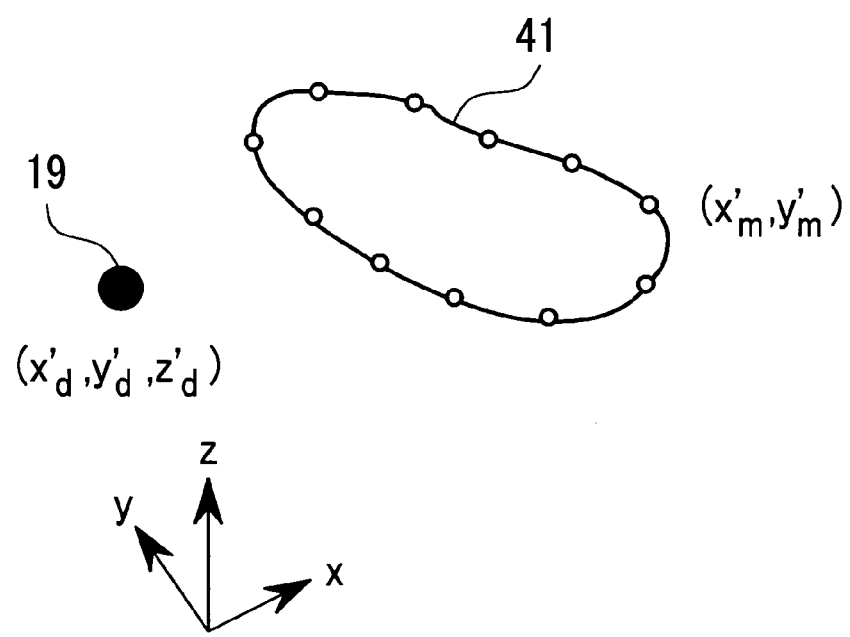
FIG. 17 illustrates a region extracted from an isointegral map and estimated coordinates of the dipole in the second embodiment of the invention.

FIG. 17 illustrates a region extracted from an isointegral map and estimated dipole coordinates, in the third embodiment of the invention.

(1) As shown in FIG. 16, the two-dimensional region 38 of $Z=Z_0$ is extracted from the three-dimensional standard heart model 15 (FIG. 14), then the coordinates 39 (($x_{0,k}$, $y_{0,k}$), k=1, 2, ..., K) of the left ventricle region consisting of DEF points are extracted. Then, the coordinates ($x_d$, $y_d$, $z_d$) of the sinus node 16 are set on the standard heart model.

(2) As shown in FIG. 17, a isointegral map during the T-wave is calculated by the expression 5 to extract the coordinates 41 (($x'_m$, $y'_m$), m=1, 2, ..., M: M=K) of a region in which the integral value exceeds a threshold value. Then, as shown in FIG. 17, dipole estimation is made using the cardiac magnetic field data at the beginning of the P-wave to obtain the dipole coordinates 19 ($x'_d$, $y'_d$, $z'_d$).

(3) A root mean square error $F_3$ is defined as expression 7. The $F_3$ is represented by the sum of a difference between the coordinates 39 ($x_{0,k}$, $Y_{0,k}$) of the left ventricle region and the coordinates 41 ($x'_m$, $y'_m$) obtained from the isointegral map 40 and a difference between the coordinates ($x_d$, $y_d$, $z_d$) of the sinus node 16 and the dipole coordinates 19 ($x'_d$, $y'_d$, $z'_d$). Then, the amount of translation ($\Delta x$, $\Delta y$) of the standard heart model that minimizes the F3 value is found. Then, the $\Delta z$ value is calculated by the expression 8. The $\Sigma$ in each of the nominator and the denominator in the expression 7 represents an addition of k=1 to K.

$$F_3(\Delta x, \Delta y) = \sqrt{\{\sum [(x_{0,k} + \Delta x - x'_k)2 + (y_{0,k} + \Delta y - y'_k)2]\}} / \quad (7)$$
$$\sqrt{\{\sum [(x'_k)2 + (y'_k)2]\}} + \sqrt{\{[(x_d + \Delta x - x'_d)2 + (y_d + \Delta y - y'_d)2]\}} / \sqrt{\{[(x'_d)2 + (y'_d)2]\}}$$

$$\Delta z = z'_d - z_d \quad (8)$$

(4) An optimal position of the standard heart model is determined using the ($\Delta x$, $\Delta y$, $\Delta z$) obtained form the expression 7 and the expression 8.

The optimal position of the standard heart model determined as described above is found to be almost the same as that in the first embodiment (FIG. 8). Both front and back CAMs are projected on the standard heart model just like that in the first embodiment. The image (obtained in the third embodiment) displayed as a synthesized result of the three-dimensional standard heart model, the front CAM, and the weighted back CAM is found to be the same as that in the first embodiment (FIG. 10). It is thus concluded that this third embodiment can also obtain the same effect as that in the first embodiment.

Next, a processing flow in the third embodiment of the invention will be described with reference to FIG. 12. Just like the first and second embodiments, at first, the processings in steps 101 to 103 are executed. And, (a) just like the processing flow in the first embodiment, in step 104-1, the coordinates of the sinus node 16 are set on the standard heart model as described with reference to FIG. 16. In step 105-1, the dipole coordinates 19 obtained from the dipole estimation of the beginning of the P-wave as described in FIG. 17 are calculated. On the other hand, just like the processing flow in the second embodiment, (b) the coordinates 39 of the left ventricle region are extracted from the three-dimensional standard heart model as described in FIG. 16 in step 104-2. Then, in step 105-2, the coordinates 41 of a region having an integral value over a threshold value is extracted from the isointegral map 40 during the T-wave as described in FIG. 17. After that, an optimal position of the standard heart model is determined using the two information items obtained in (a) and (b).

The processings in steps 107 to 109 are the same as those in the first and second embodiments, so that the description for them will be omitted here.

Fourth Embodiment

In this fourth embodiment, the base levels of both front and back current values are adjusted using a weight coefficient W that equalizes the CAMs of outline of both (front and back) measurement planes. Concretely, the base levels of the front and back CAM current values are adjusted into one in the following five processing steps.

Figure 18:
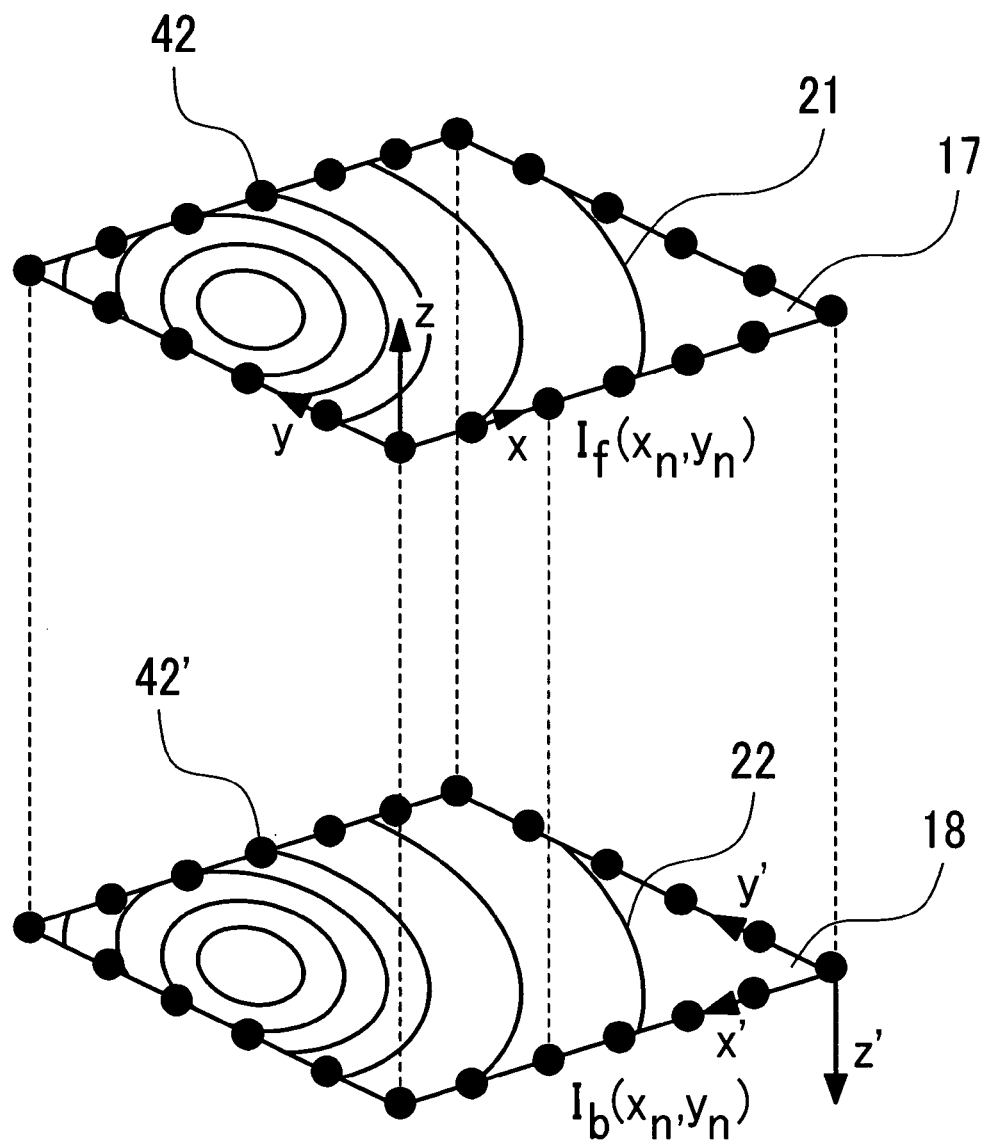
FIG. 18 illustrates a method for calculating a weight coefficient W in the fourth embodiment of the invention.

FIG. 18 illustrates a method for calculating a weight coefficient W in the fourth embodiment of the invention.

(1) As shown in FIG. 18, the amplitude If ($x_n$, $y_n$) (n=1, 2, ..., N) of the CA on the measurement point 42 at the outline of the front measurement surface 17 is extracted.

(2) As shown in FIG. 18, the amplitude $I_b$ ($x_n$, $y_n$) (n=1, 2, ..., N) of the CA on the measurement point 42' at the amplitude of the back measurement surface 18 is calculated.

(3) A weight coefficient W that minimizes the result of the expression 9 is calculated using $I_f(x_n, y_n)$ and $I_b(x_n, y_n)$. The $\Sigma$ represents an addition of n=1 to N.

$$F(W) = \Sigma (I_f(x_n,y_n) - W \times I_b(x_n,y_n))^2 \quad (9)$$

(4) the expression 9 is calculated for time over one heartbeat or the total measurement time and optimal weight coefficient is determined by W with minimum value of F(W).

(5) The front CAM and the weighted back CAM are projected on the standard heart model. However, in order to obtain continuous current distributions more effectively, an interpolation region is set near the junction region of the front and back surface of the standard heart model.

In this fourth embodiment, the optimal position of the standard heart model is determined using one of the three positional adjustment methods in the first to third embodiments. The image displayed as a result of the visualization of cardiac electrical current distribution with the three-dimensional model in the fourth embodiment is found to be the same as that in the first embodiment (FIG. 10). It is thus concluded that this fourth embodiment can also obtain the same effect as that in the first embodiment.

Fifth Embodiment

In the fifth embodiment, the measurement region is extended and both front and back current distributions and the distributions of the amplitudes of those current distributions corresponding to the extended region are obtained through spline interpolation, then both front and back current distributions and distributions of the amplitudes of those current distributions are projected on the standard heart model together with the extended region.

Figure 19:
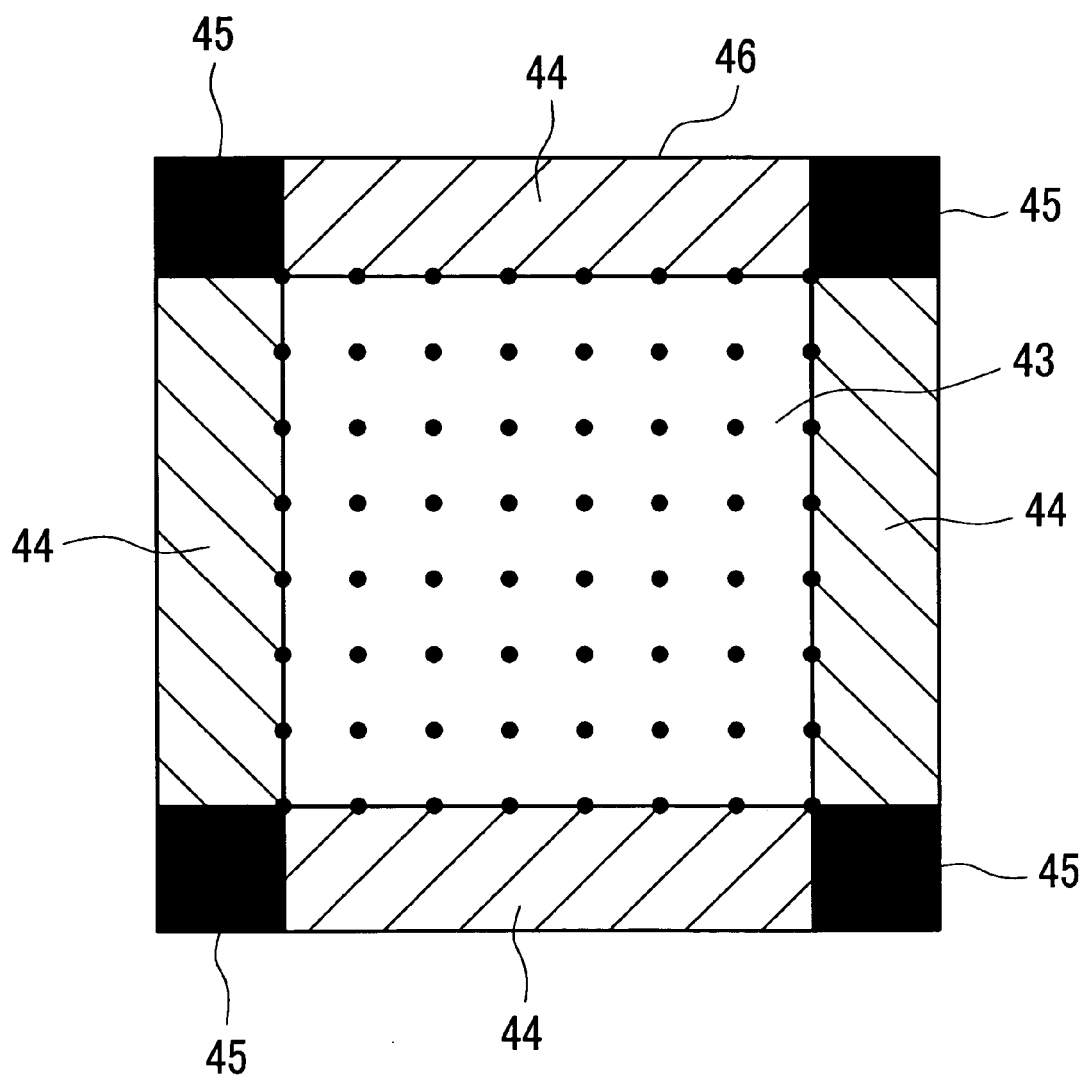
FIG. 19 illustrates a measurement plane and a plane to be expanded in the fifth embodiment of the invention.

FIG. 19 illustrates a measurement region and a region to be extended in the fifth embodiment of the invention. The standard heart model is not always included in the measurement region 43 (a region in which heart magnetic field data is measured) when an optimal position of the standard heart model is determined in the first to fourth embodiments. In that case, it is difficult to obtain current distributions and distributions of the amplitudes of those current distributions for outside of the measurement region 43.

To avoid such a trouble, virtually extended regions 44 and 45 are set to extend the measurement region 43. Each of the regions 44 and 45 is assumed to include a plurality of magnetometers disposed just like the measurement region 43. The current distributions and the distributions of the amplitudes of those current distributions corresponding to the extended regions 44 and 45 are obtained through spline interpolation using the magnetic field data measured in the measurement region 43. In such a way, current distributions corresponded to the extended region are obtained.

In the fifth embodiment, the optimal position of the standard heart model is determined using any of the positional adjustment methods in the first to third embodiments.

Both front and back extended current distributions and distributions of the amplitudes of those current distributions are projected on the standard heart model using any of the methods in the first and fourth embodiments. The image displayed in the fifth embodiment as a result of visualization of the cardiac electrical current with, as well as both front and weighted back current distributions and distributions of the amplitudes of those current distributions is found to be the same as that in the first embodiment (FIG. 10). This is why this fifth embodiment can also obtain the same effect as that in the first embodiment.

Sixth Embodiment

Figure 20:
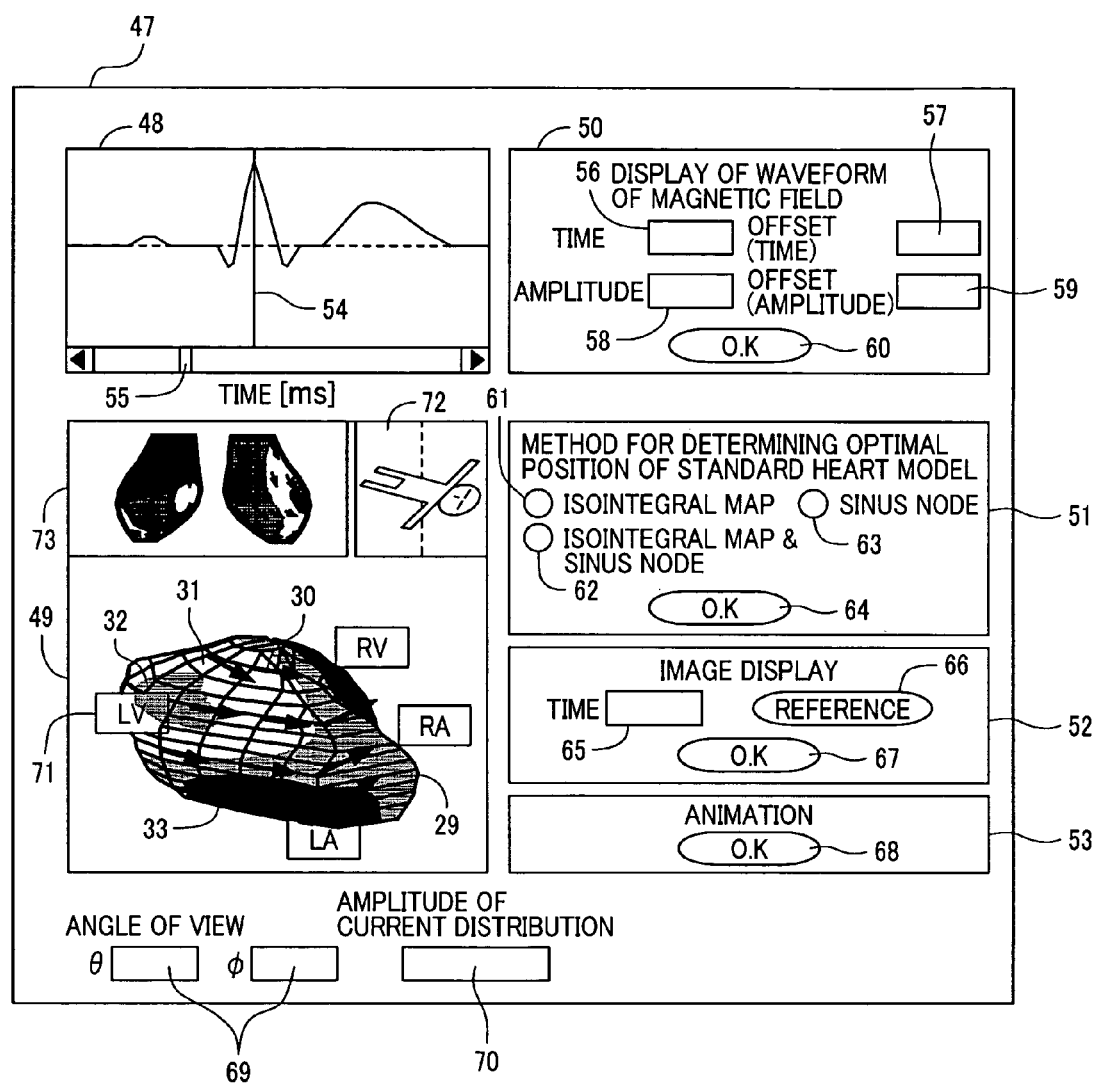
FIG. 20 illustrates a result of projection of current distributions and distributions of the amplitudes of those current distributions on a standard heart model and an example of a screen display of a computer in the sixth embodiment of the invention.

FIG. 20 illustrates a result of projection of the current distributions and the distributions of the amplitudes of those current distributions on a standard heart model, in the sixth embodiment of the invention. FIG. 20 shows a screen example 47 to be displayed on the display device of the computer 7 of a biomagnetic measurement apparatus.

The screen 47 of the computer 7 comprises a screen 48 for displaying one or a plurality of magnetic field waveforms measured by a plurality of magnetometers and a screen 49 for displaying cardiac electrical current distributions projected on a standard heart model.

The screen 47 comprises a setting screen 50 for setting display of magnetic waveforms to be displayed on the screen 48, a selection screen 51 for selecting a method for adjusting the optimal position of a standard heart model, a display screen 52 for displaying an image of cardiac electrical current distributions obtained by synthesizing a standard heart model, current vectors, and distributions of the amplitudes of those current vectors, and an execution screen 53 for executing an animation of cardiac electrical current distributions.

The setting screen 50 includes an input field 56 for setting a time width of a waveform to be displayed, an input field 57 for setting a time offset, an input field 58 for setting an amplitude of a waveform to be displayed, an input field 59 for setting an amplitude offset, and an OK button 60 for reflecting the data set in each of the input fields 56 to 59 onto the display screen 48.

The selection screen 51 includes radio buttons 61 to 63 for selecting three methods for adjusting the optimal position of a standard heart model and an OK button 64 for executing any of the three methods selected by one of the radio buttons 61 to 63. The radio button 61 selects a method for determining an optical position of a standard heart model according to an isointegral map. The radio button 62 selects a method for determining an optical position of a standard heart model according to an isointegral map and a sinus node. The radio button 63 selects a method for determining an optical position of a standard heart model according to a sinus node.

The setting screen 52 includes an input field 65 for setting a time instant to display a cardiac-current distribution and an OK button 67 for displaying a bar, which reflect the time instant in input field 65, onto the screen 49.

The display screen 53 includes an OK button 68 for executing an animation.

The display screen 49 includes input fields 69 for adjusting the angle of the view of the cardiac electrical current image and an input field 70 for selecting the display range of the amplitude of the current distributions 31, 32, and 33.

The display screen 48 also includes a scroll bar 55 corresponding to a displayed time of a cardiac magnetic field waveform and a bar 54 to be displayed when the button 66 on the display screen 52 is pressed.

The display screen 49 also includes a box 71 for displaying RA, LA, RV, and LV for the regions of the right atrium, the left atrium, the right ventricle, and the left ventricle of the standard heart model, as well as a screen 72 for displaying a guide of the angle of the view to facilitate the user to make it easier whereby to understand the view point of the standard heart model. The guides on the screens 71 and 72 are automatically changed in response to each change of the display angle of the standard heart model. The display screen 49 also includes a screen 73 for displaying cardiac electrical current distribution images (as shown in FIGS. 10C and 10D) in both plus and minus directions of the x axis as described above and cardiac-current distribution images (as shown in FIGS. 10B and 10A) in both plus and minus directions of the z axis. Next, a description will be made for the display of cardiac electrical current distributions projected on the standard heart model at a given view.

Figure 21:
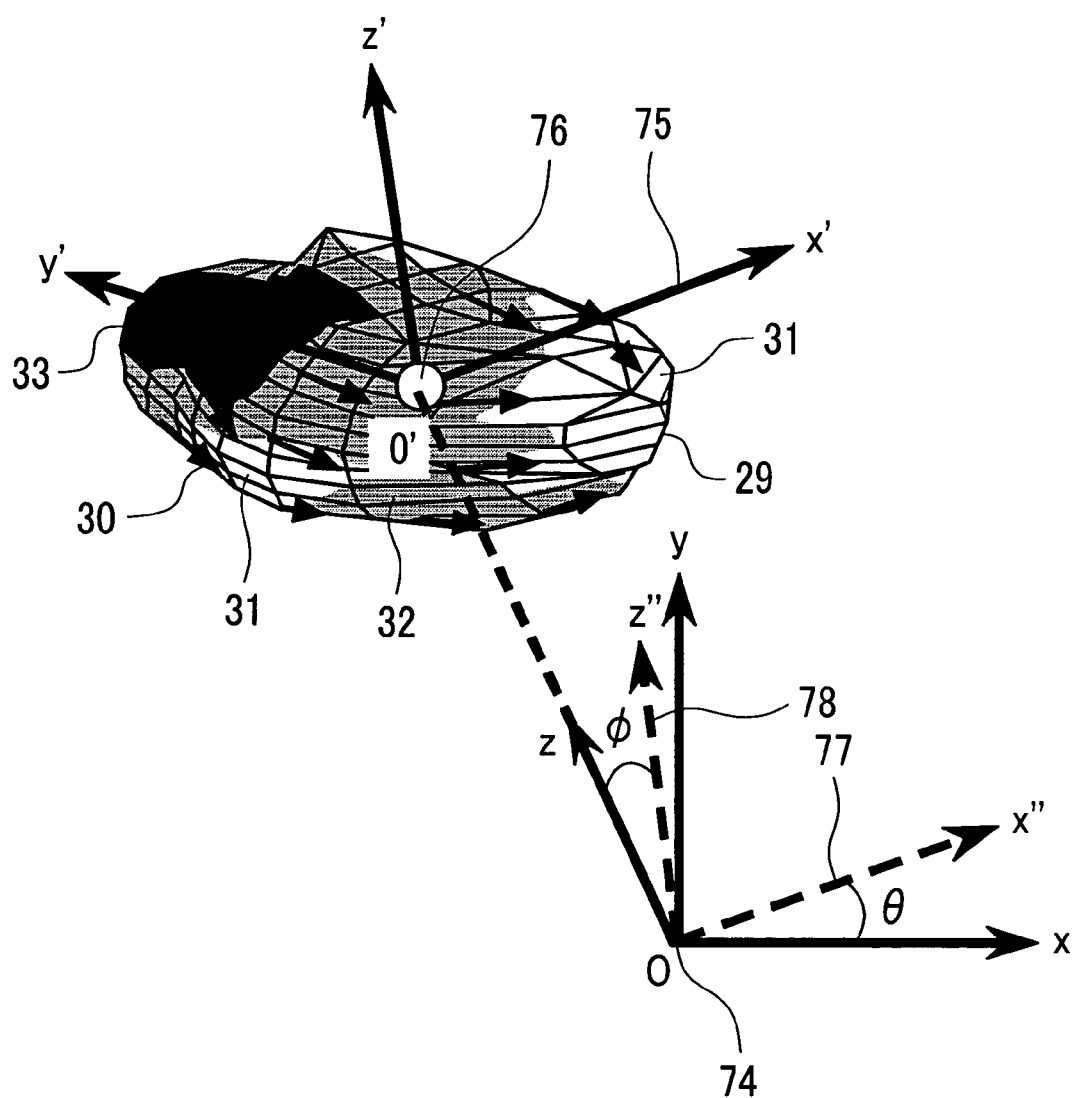
FIG. 21 illustrates angles θ and φ at a viewpoint in the sixth embodiment of the invention.

FIG. 21 illustrates angles θ and φ at a given view point in the sixth embodiment of the invention.

The coordinate system 74 denotes a viewpoint coordinate system. The coordinate system 75 denotes a coordinate system of the standard heart model 29. The origin O' of the coordinate system 74 of the standard heart model 29 is disposed at the center point 76 of the model. The x' axis that is moved, in parallel, up to the viewpoint O along a line between the viewpoint O (given) and the center point 76 is assumed as an x" axis 77. The z' axis, after it is moved in parallel similarly, is assumed as a z" axis 78. At that time, an angle made by the x axis and the x" axis is assumed as θ. The angle made by the z axis and the z" axis is assumed as φ, respectively. Next, a description will be made for how to display cardiac-current distributions projected on the standard heart model at a given view after the coordinate system 75 of the standard heart model 29 is disposed at the top end of the model 29.

Figure 22:
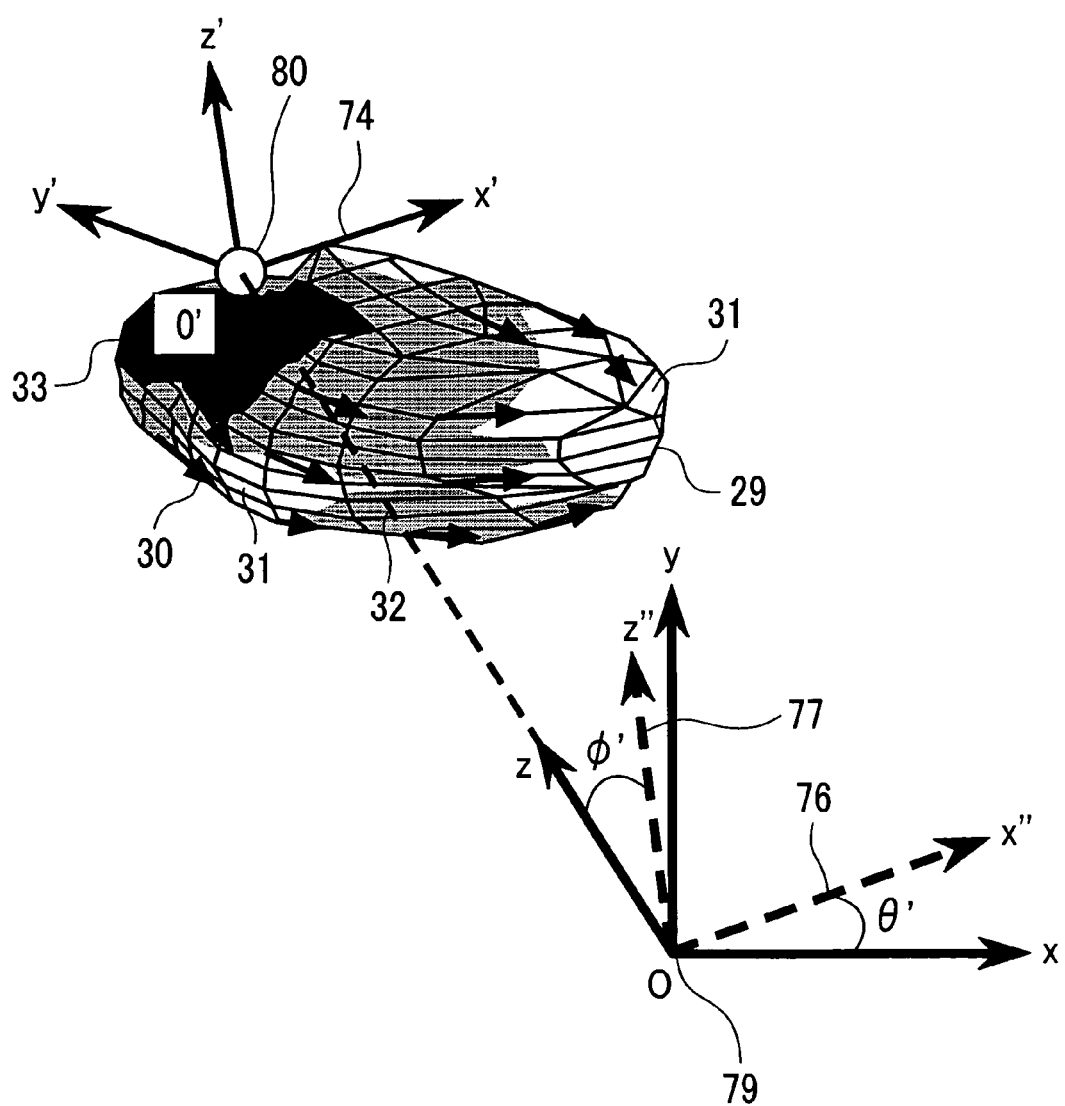
FIG. 22 illustrates angles θ' and φ' at a viewpoint in the sixth embodiment of the invention.

FIG. 22 illustrates angles θ' and φ' at a given viewpoint in the sixth embodiment of the invention.

The coordinate system 79 denotes a viewpoint coordinate system. The coordinate system 74 denotes a coordinate system of the standard heart model 29. The origin O' of the coordinate system 74 of the standard heart model 29 is disposed at the top end point 80 of the model. The x' axis that is moved, in parallel, up to the viewpoint O along a line between the viewpoint O (given) and the top end point 80 of the standard heart model 29 is assumed as an X" axis 76. The z' axis, after it is moved in parallel similarly, is assumed as a z" axis 77. At that time, an angle made by the x axis and the x" axis is assumed as θ'. The angle made by the z axis and the z" axis is assumed as φ', respectively.

The viewpoint shown in FIG. 10 assumed as a result of the image display in the first embodiment, as well as the viewpoint of the standard heart model displayed on the screen 49 for displaying cardiac electrical current distributions in the sixth embodiment are the same as those displayed when the origin O' of the coordinate system 73 of the standard heart model 29 at the center point 76 of the model 29. At that time, the respective viewpoints (θ, φ) shown in FIGS. 10A, 10B, 10C, and 10D are similar to each of (0°, 0°), (−180°, 0°), (0°, −90°), and (0°, 90°). The viewpoint (θ, φ) of the standard heart model in the sixth embodiment is similar to (−100°, −160°).

As described above, the invention enables analysis of cardiac magnetic field measured from two directions with simple operations.

Seventh Embodiment

In the seventh embodiment, each standard heart model is created from chest image obtained by a fluoroscopic CT apparatus and a fluoroscopic photographing apparatus. The optimal position of the standard heart model is determined using any of the methods employed in the first to third embodiments. Similarly, any of the methods employed in the first, fourth, and fifth embodiments can be used to project both front and back CAMs on the standard heart model. The image displayed in the seventh embodiment as a synthesized result of the three-dimensional standard heart model, the front and weighted back current distributions, and the amplitudes of the front and weighted back current distributions is found to be the same as that (FIG. 10) in the first embodiment. This is why the seventh embodiment can also obtain the same effect as that in the first embodiment.

Eighth Embodiment

In this eighth embodiment, standard heart models are created by simulating both size and shape of an averaged heart in each generation using chest image data of healthy subjects in each generation photographed by a nuclear magnetic resonance imaging apparatus, a fluoroscopic CT apparatus, and a fluoroscopic photographing apparatus. When current distribution images are projected on such a standard heart model, optimal standard heart model is selected from each generation heart model. The optimal position of the standard heart model is determined by any of the methods employed in the first through third embodiments.

Both front and back CAMs are projected on the standard heart model using any of the methods employed in the first, fourth, and fifth embodiments. The image displayed in the eighth embodiment as a synthesized result of the three-dimensional standard heart mode, front and weighted back current distribution images, and the amplitudes of the front and weighted back current distributions is found to be the same as that (FIG. 10) in the first embodiment. This is why the eighth embodiment can also obtain the same effect as that in the first embodiment.

Hereunder, a description will be made for a embodiment of a biomagnetic measurement apparatus capable of projecting both front and back current distributions, as well as the distributions of the amplitudes of those current distributions, on the three-dimensional heart model of each subject continuously.

Ninth Embodiment

This ninth embodiment describes a case in which a heart model is created from MRI images of each subject and the created model is used instead of the standard heart model. At that time, each outline points of the created heart model corresponds to the coordinate system of the MRI images. Therefore, the coordinates 11 of the xiphoid process in the coordinate system of the MRI shown in FIG. 4 and the coordinates 11 of the xiphoid process in the coordinate system of the biomagnetic measurement apparatus shown in FIG. 2 are assumed as reference points to convert coordinates of each outline points to coordinates of the coordinate system of the biomagnetic measurement apparatus. Consequently, an optimal position of the heart model is determined.

Both front and back CAMs can be projected on the heart model of each subject using any of the methods employed in the first, fourth, and fifth embodiments.

FIG. 23 is an example of projection of weighted current distributions in the ninth embodiment of the invention. Concretely, the front CAM and the back CAM, which weighted by a coefficient W, at the beginning of the P-wave are projected on the heart model 81 of each subject. The subject is the same as that (FIG. 10) in the first embodiment. FIG. 23A is a back projection view, FIG. 23B is a front projection view, FIG. 23C is a right hand side view, and FIG. 23D is a left hand side view of the heart model of each subject after the above projection. In FIGS. 23A through 23D, each arrow denotes a current vector 82 as follows; white region 83 denotes a region in which the amplitude of the current vector is small, gray region 84 denotes a region in which the amplitude of the current vector is medium, and black region 85 denotes a region in which the amplitude of the current vector is large, respectively.

Figure 23A:
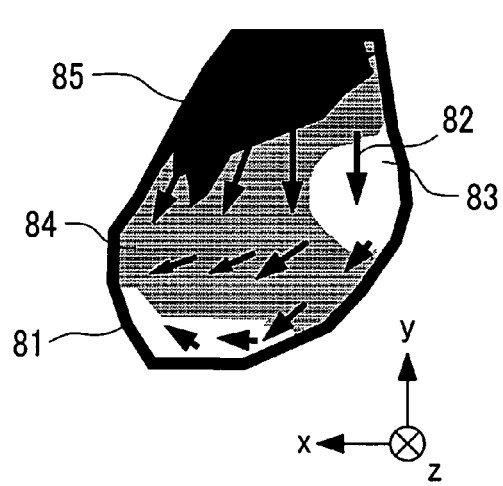
FIG. 23 illustrates a result of a projection of front CAM and weighted back CAM on a heart model for a subject in the ninth embodiment of the invention.
Figure 23B:
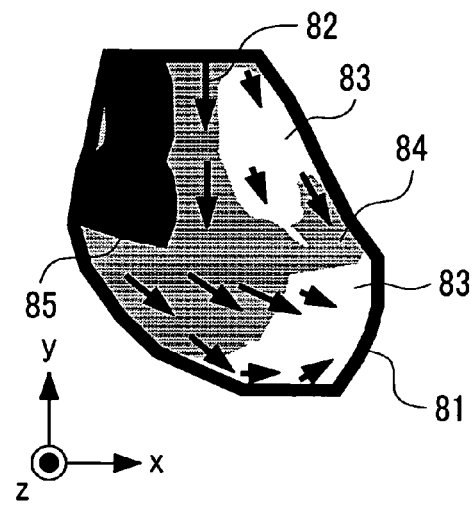
Figure 23C:
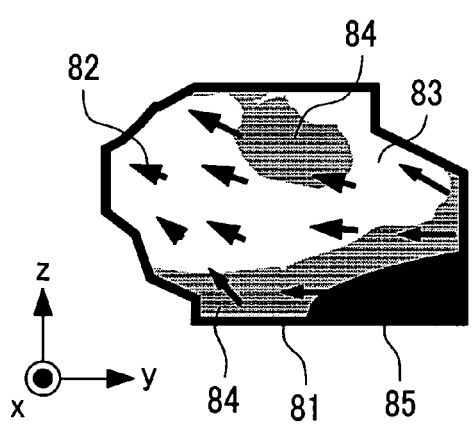
Figure 23D:
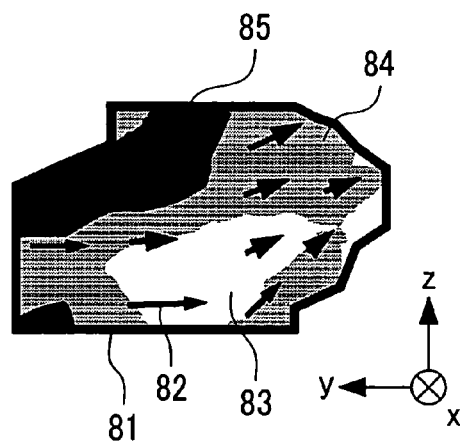

As described in the first embodiment, the heart muscle excitement at the beginning of the P-wave is in an atrium excitement. The left atrium excitement becomes rather stronger than that of the right atrium. As shown in FIGS. 23A and 23B, both right and left atriums are large current regions. In particular, the excitement in the left atrium is found to be more significant than that in the right atrium. As shown in FIGS. 23C and 23D, both front CAM and the back CAM weighted by a coefficient W projected on the heart model of each subject denote continuous current distributions. As to be understood from the above description, cardiac electrical current distribution images are obtained in accordance with the electrophysiological phenomena of the subject heart by adjusting the base levels of the current values into one just like the result shown in FIG. 23.

As described above, the biomagnetic measurement apparatus of the invention, therefore, can project both front and back current distributions and the distributions of the amplitudes of those distributions seamlessly, on each three-dimensional standard heart model, and thereby visualizing the cardiac-current distributions conforming to the cardiac morphology of each subject.

What is claimed is:

1. A biomagnetic measuring system comprising:
   a plurality of magnetometers, each adapted to be disposed two-dimensionally at a position of (x, y) coordinates in parallel to the chest surface of a living body and used for measuring a time change of a magnetic field component in a z direction vertical to an xy plane of a biomagnetic field to be generated from the living body or time changes of magnetic components in both x and y directions in parallel to the xy plane from two opposing directions;
   a calculating device for calculating an output signal from each of said plurality of magnetometers used for measurements in the two opposing directions; and
   a display device for displaying a result of the calculation;
   wherein said calculating device performs:
   (1) calculations to obtain current distributions in the two directions from the output signals and/or to obtain distributions of the amplitudes of those current distributions;
   (2) a calculation to obtain an isointegral map according to the output signals in a predetermined period, and to obtain a region having an isointegral map value exceeding a predetermined threshold value;
   (3) a calculation to estimate the amplitude, direction, and position of one current source, from the output signal at a predetermined point of time;
   (4) a calculation to convert data so as to determine an optimal position for displaying the data that represents a three-dimensional heart model simulating a heart shape, and current distributions in the two directions and/or distributions of the amplitudes of those current distributions obtained in the calculation (1), using the result obtained from at least one of the calculations (2) and (3);

(5) a calculation to adjust the base levels of current values into one with respect to position-adjusted current distributions in the two directions and/or distributions of the amplitudes of those current distributions; and (6) a calculation to obtain synthesized image data obtained by projecting the base-level-adjusted current distributions in the two directions and/or the distributions of the amplitudes of those current distributions, from the z direction, on a position denoted by the (x, y) coordinates of the data representing the three-dimensional heart model, and wherein the synthesized image data is displayed two-dimensionally or three-dimensionally on said display device.

2. The apparatus according to claim 1, wherein the predetermined period is defined as a period in which a T wave appears.

3. The apparatus according to claim 1, wherein the predetermined point of time is defined as a starting point of a P wave.

4. A biomagnetic measuring system comprising:

a plurality of magnetometers, each adapted to be disposed two-dimensionally at a position of (x, y) coordinates in parallel to the chest surface of a living body and used for measuring a time change of a magnetic field component in a z direction vertical to an xy plane of a biomagnetic field to be generated from the living body or time changes of magnetic comnonents in both x and y directions in parallel to the xy plane from two opposing directions;

a calculating device for calculating an output signal from each of said plurality of magnetometers used for measurements in the two opposing directions; and a display device for displaying a result of the calculation;

wherein said calculating device performs:

(1) calculations to obtain current distributions in the two directions from the output signals and/or to obtain distributions of the amplitudes of those current distributions:

(2) a calculation to obtain an isointegral man according to the output signals in a predetermined period, and to obtain a region having an isointegral map value exceeding a predetermined threshold value;

(3) a calculation to estimate the amplitude, direction, and position of one current source, from the output signal at a predetermined point of time;

(4) a calculation to convert data so as to determine an optimal position for displaying the data that represents a three-dimensional heart model simulating a heart shape, and current distributions in the two directions and/or distributions of the amplitudes of those current distributions obtained in the calculations (1), using the result obtained from at least one of the calculation (2) and (3);

(5) a calculation to adiust the base levels of current values into one with respect to position-adjusted current distributions in the two directions and/or distributions of the amplitudes of those current distributions; and (6) a calculation to obtain synthesized image data obtained by projecting the base-level-adjusted current distributions in the two directions and/or the distributions of the amplitudes of those current distributions, from the z direction, on a position denoted by the (x, y) coordinates of the data representing the three-dimensional heart model, wherein the synthesized image data is displayed two-dimensionally or three-dimensionally on said display device, and wherein said calculating device calculates a weight coefficient that enables the current distributions in the two directions and/or distributions of the amplitudes of those current distributions obtained in the calculation (1), to be aligned most with each other at a position denoted by the (x, y) coordinates of boundary data of the outline of the data representing the three-dimensional heart model, viewed from the z direction, and then to make the calculation(5).

5. A biomagnetic measuring system comprising:

a plurality of magnetometers, each adapted to be disposed two-dimensionally at a position of (x, y) coordinates in parallel to the chest surface of a living body and used for measuring a time change of a magnetic field component in a z direction vertical to an xy plane of a biomagnetic field to be generated from the living body or time changes of magnetic components in both x and y directions in parallel to the xy plane from two opposing directions;

a calculating device for calculating an output signal from each of said plurality of magnetometers used for measurements in the two opposing directions; and a display device for displaying a result of the calculation;

wherein said calculating device performs;

(1) calculations to obtain current distributions in the two directions from the output signals and/or to obtain distributions of the amplitudes of those current distributions;

(2) a calculation to obtain an isointegral map according to the output signals in a predetermined period, and to obtain a region having an isointegral map value exceeding a predetermined threshold value;

(3) a calculation to estimate the amplitude, direction, and position of one current source, from the output signal at a predetermined point of time;

(4) a calculation to convert data so as to determine an optimal position for displaying the data that represents a three-dimensional heart model simulating a heart shape, and current distributions in the two directions and/or distributions of the amplitudes of those current distributions obtained in the calculation (1), using the result obtained from at least one of the calculations (2) and (3);

(5) a calculation to adjust the base levels of current values into one with respect to position-adjusted current distributions in the two directions and/or distributions of the amplitudes of those current distributions; and (6) a calculation to obtain synthesized image data obtained by projecting the base-level-adjusted current distributions in the two directions and/or the distributions of the amplitudes of those current distributions, from the z direction, on a position denoted by the (x, y) coordinates of the data representing the three-dimensional heart model, wherein the synthesized image data is displayed two-dimensionally or three-dimensionally on said display device, and wherein said calculating device calculates a weight coefficient that enables the current distributions in the two directions and/or the distributions of the amplitudes of those current distributions, obtained in the calculation (1), to be aligned most with each other at a boundary between those distributions, and to make the calculation in the calculation(5).

6. A biomagnetic measuring system comprising;
a plurality of magnetometers, each adapted to be disposed two-dimensionally at a position of (x, y) coordinates in parallel to the chest surface of a living body and used for measuring a time change of a magnetic field component in a z direction vertical to an xy plane of a biomagnetic field to be generated from the living body or time changes of magnetic components in both x and y directions in parallel to the xy plane from two opposing directions;
a calculating device for calculating an output signal from each of said plurality of magnetometers used for measurements in the two opposing directions; and
a display device for displaying a result of the calculation;
wherein said calculating device performs;
(1) calculations to obtain current distributions in the two directions from the output signals and/or to obtain distributions of the amplitudes of those current distributions;
(2) a calculation to obtain an isointegral map according to the output signals in a predetermined period, and to obtain a region having an isointegral map value exceeding a predetermined threshold value;
(3) a calculation to estimate the amplitude, direction, and position of one current source, from the output signal at a predetermined point of time;
(4) a calculation to convert data so as to determine an optimal position for displaying the data that represents a three-dimensional heart model simulating a heart shape, and current distributions in the two directions and/or distributions of the amplitudes of those current distributions obtained in the calculation (1), using the result obtained from at least one of the calculations (2) and (3);
(5) a calculation to adjust the base levels of current values into one with respect to position-adjusted current distributions in the two directions and/or distributions of the amplitudes of those current distributions; and
(6) a calculation to obtain synthesized image data obtained by projecting the base-level-adjusted current distributions in the two directions and/or the distributions of the amplitudes of those current distributions, from the z direction, on a position denoted by the (x, y) coordinates of the data representing the three-dimensional heart model,
wherein the synthesized image data is displayed two-dimensionally or three-dimensionally on said display device, and
wherein said calculating device in the calculation(4) adjusts the position of a sinus node and the estimated position of the current source so as to minimize the difference between the sinus node position and the estimated current source position in the data representing the three-dimensional heart model.

7. The apparatus according to claim 6,
wherein said calculating device sets a virtual extended region in which existence of a plurality of magnetometers disposed under the same condition as that of said plurality of magnetometers in the measurement region is assumed outside the measurement region of the biomagnetic field, to obtain output signals from said plurality of magnetometers in the extended region by extrapolating those signals, and then to perform at least one of the calculations.

8. The apparatus according to claim 6,
wherein said display device is so designed as to display buttons for the selection of the calculations and to do the calculation selected.

9. The apparatus according to claim 6,
wherein said display device is so designed as to display the synthesized image data and the output signals from said plurality of magnetometers simultaneously.

10. The apparatus according to claim 6,
wherein said display device is so designed as to display the synthesized image data three-dimensionally, at the same time to display the name of each tissue of a subject's heart on the three-dimensional synthesized data image.

11. The apparatus according to claim 6,
wherein three-dimensional image data to be obtained by a magnetic resonance imaging apparatus or X-ray computed tomography apparatus is used as the data representing the three-dimensional heart model.

12. The apparatus according to claim 6,
wherein said display device is so designed as to display the synthesized image data, viewed from both plus and minus directions of the z direction, two-dimensionally or three-dimensionally.

13. The apparatus according to claim 6,
wherein said display device is so designed as to display the synthesized image data, viewed from both plus and minus directions of the x direction, two-dimensionally or three-dimensionally.

14. A biomagnetic measuring system comprising;
a plurality of magnetometers, each adapted to be disposed two-dimensionally at a position of (x, y) coordinates in parallel to the chest surface of a living body and used for measuring a time change of a magnetic field component in a z direction vertical to an xy plane of a biomagnetic field to be generated from the living body or time changes of magnetic components in both x and y directions in parallel to the xy plane from two opposing directions;
a calculating device for calculating an output signal from each of said plurality of magnetometers used for measurements in the two onnosing directions; and
a display device for displaying a result of the calculation;
wherein said calculating device performs;
(1) calculations to obtain current distributions in the two directions from the output signals and/or to obtain distributions of the amplitudes of those current distributions;
(2) a calculation to obtain an isointegral map according to the output signals in a predetermined period, and to obtain a region having an isointegral map value exceeding a predetermined threshold value;
(3) a calculation to estimate the amplitude, direction, and position of one current source, from the output signal at a predetermined point of time;
(4) a calculation to convert data so as to determine an optimal position for displaying the data that represents a three-dimensional heart model simulating a heart shape, and current distributions in the two directions and/or distributions of the amplitudes of those current distributions obtained in the calculation (1), using the result obtained from at least one of the calculations (2) and (3);

(5) a calculation to adjust the base levels of current values into one with respect to position-adjusted current distributions in the two directions and/or distributions of the amplitudes of those current distributions; and (6) a calculation to obtain synthesized image data obtained by projecting the base-level-adjusted current distributions in the two directions and/or the distributions of the amplitudes of those current distributions, from the z direction, on a position denoted by the (x, y) coordinates of the data representing the three-dimensional heart model, wherein the synthesized image data is displayed two-dimensionally or three-dimensionally on said display device, and wherein said calculating device in the calculation(4) adjusts the positions of the region of the left ventricle and a region having an isointegral map value exceeding the predetermined threshold value so as to minimize the difference between the left ventricle region and the region having an isointegral value exceeding the set threshold value in the data representing the three-dimensional heart model.

15. The apparatus according to claim 14, wherein said calculating device sets a virtual extended region in which existence of a plurality of magnetometers disposed under the same condition as that of said plurality of magnetometers in the measurement region is assumed outside the measurement region of the biomagnetic field, to obtain output signals from said plurality of magnetometers in the extended region by extrapolating those signals, and then to perform at least one of the calculations.

16. A biomagnetic measuring system comprising;

a plurality of magnetometers, each adapted to be disposed two-dimensionally at a position of (x, y) coordinates in parallel to the chest surface of a living body and used for measuring a time change of a magnetic field component in a z direction vertical to an xy plane of a biomagnetic field to be generated from the living body or time changes of magnetic components in both x and y directions in parallel to the xy plane from two opposing directions;

a calculating device for calculating an output signal from each of said plurality of magnetometers used for measurements in the two opposing directions; and a display device for displaying a result of the calculation;

wherein said calculating device performs:

(1) calculations to obtain current distributions in the two directions from the output signals and/or to obtain distributions of the amplitudes of those current distributions;

(2) a calculation to obtain an isointegral map according to the output signals in a predetermined period, and to obtain a region having an isointegral map value exceeding a predetermined threshold value;

(3) a calculation to estimate the amplitude, direction, and position of one current source, from the output signal at a predetermined point of time;

(4) a calculation to convert data so as to determine an optimal position for displaying the data that represents a three-dimensional heart model simulating a heart shape, and current distributions in the two directions and/or distributions of the amplitudes of those current distributions obtained in the calculation (1), using the result obtained from at least one of the calculations (2) and (3);

(5) a calculation to adjust the base levels of current values into one with respect to position-adjusted current distributions in the two directions and/or distributions of the amplitudes of those current distributions; and (6) a calculation to obtain synthesized image data obtained by projecting the base-level-adjusted current distributions in the two directions and/or the distributions of the amplitudes of those current distributions, from the z direction, on a position denoted by the (x, y) coordinates of the data representing the three-dimensional heart model, wherein the synthesized image data is displayed two-dimensionally or three-dimensionally on said display device, and wherein said calculating device in the calculation(4) adjusts the position of the sinus node and the estimated position of the current source, as well as positions of the left ventricle region and the region having an isointegral map value exceeding the set threshold value so as to minimize the difference between the sinus node position and the estimated position of the current source, as well as the difference between the left ventricle region and the region having an isointegral map value exceeding the set threshold value in the data representing the three-dimensional heart model, respectively.

17. The apparatus according to claim 16, wherein said calculating device sets a virtual extended region in which existence of a plurality of magnetometers disposed under the same condition as that of said plurality of magnetometers in the measurement region is assumed outside the measurement region of the biomagnetic field, to obtain output signals from said plurality of magnetometers in the extended region by extrapolating those signals, and then to perform at least one of the calculations.

* * * * *

UNITED STATES PATENT AND TRADEMARK OFFICE
CERTIFICATE OF CORRECTION

| | | |
|---|---|---|
| PATENT NO. | : 7,363,070 B2 | Page 1 of 1 |
| APPLICATION NO. | : 10/875281 | |
| DATED | : April 22, 2008 | |
| INVENTOR(S) | : Ogata et al. | |

It is certified that error appears in the above-identified patent and that said Letters Patent is hereby corrected as shown below:

On the cover page, item 30; should read

(30)   Foreign Application Priority Data

~~Dec.~~ Sep. 10, 2003   (JP)   .................................. 2003-317705

Signed and Sealed this

Twelfth Day of August, 2008

JON W. DUDAS
*Director of the United States Patent and Trademark Office*